(12) United States Patent
Kamioka et al.

(10) Patent No.: US 11,325,921 B2
(45) Date of Patent: May 10, 2022

(54) OPTICALLY ACTIVE CROSSLINKED CYCLIC SECONDARY AMINE DERIVATIVE

(71) Applicant: Sumitomo Dainippon Pharma Co., Ltd., Osaka (JP)

(72) Inventors: Seiji Kamioka, Toyonaka (JP); Naoaki Shimada, Takatsuki (JP); Wataru Hirose, Suita (JP); Hitoshi Ban, Nishinomiya (JP); Akihiko Yokoyama, Tsuruoka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 46 days.

(21) Appl. No.: 17/042,479

(22) PCT Filed: Mar. 29, 2019

(86) PCT No.: PCT/JP2019/013941
§ 371 (c)(1),
(2) Date: Sep. 28, 2020

(87) PCT Pub. No.: WO2019/189732
PCT Pub. Date: Oct. 3, 2019

(65) Prior Publication Data
US 2021/0024547 A1 Jan. 28, 2021

(30) Foreign Application Priority Data
Mar. 30, 2018 (JP) .............................. JP2018-067187

(51) Int. Cl.
| | | |
|---|---|---|
| C07D 519/00 | (2006.01) | |
| A61K 45/06 | (2006.01) | |
| A61K 31/439 | (2006.01) | |
| A61P 35/00 | (2006.01) | |
| A61P 35/02 | (2006.01) | |

(52) U.S. Cl.
CPC ............ C07D 519/00 (2013.01); *A61K 45/06* (2013.01)

(58) Field of Classification Search
CPC .... C07D 519/00; A61K 45/06; A61K 31/439; A61P 35/00; A61P 35/02
See application file for complete search history.

(56) References Cited

U.S. PATENT DOCUMENTS

| | | |
|---|---|---|
| 2011/0065690 A1 | 3/2011 | Grembecka et al. |
| 2014/0275070 A1 | 9/2014 | Grembecka et al. |
| 2014/0371239 A1 | 12/2014 | Grembecka et al. |
| 2017/0247391 A1 | 8/2017 | Grembecka et al. |
| 2018/0105531 A1 | 4/2018 | Grembecka et al. |
| 2018/0243303 A1 | 8/2018 | Grembecka et al. |
| 2019/0010167 A1 | 1/2019 | Claremon et al. |
| 2019/0092783 A1 | 3/2019 | Wu et al. |
| 2019/0092784 A1 | 3/2019 | Wu et al. |
| 2019/0144459 A1 | 5/2019 | Cacatian et al. |
| 2019/0152947 A1 | 5/2019 | Wang et al. |
| 2019/0202830 A1 | 7/2019 | Cacatian et al. |
| 2019/0315758 A1 | 10/2019 | Li et al. |

FOREIGN PATENT DOCUMENTS

| | | |
|---|---|---|
| CN | 106831787 A | 6/2017 |
| JP | 2016-512514 | 4/2016 |
| WO | WO 2011/029054 A1 | 3/2011 |
| WO | WO 2014/164543 A1 | 10/2014 |
| WO | WO 2016/040330 A1 | 3/2016 |
| WO | WO 2016/195776 A1 | 12/2016 |
| WO | WO 2016/197027 A1 | 12/2016 |
| WO | WO 2017/112768 A1 | 6/2017 |
| WO | WO 2017/161002 A1 | 9/2017 |
| WO | WO 2017/161028 A1 | 9/2017 |
| WO | WO 2017/192543 A1 | 11/2017 |

(Continued)

OTHER PUBLICATIONS

Grembecka J., et al.; "Menin-MLL inhibitors reverse oncogenic activity of MLL fusion proteins in leukemia"; Nature Chemical Biology, vol. 8; Mar. 2012; pp. 277-284.
Borkin D., et al.; "Pharmacologic Inhibition of the Menin-MLL Interaction Blocks Progression of MLL Leukemia In Vivo"; Cancer Cell 27; Apr. 13, 2015; pp. 589-602.
Borkin D., et al.; "Property Focused Structure-Based Optimization of Small Molecule Inhibitors of the Protein-Protein Interaction between Menin and Mixed Lineage Leukemia (MLL)"; J. Med. Chem., 59; (2016); pp. 892-913.
Xu S., et al.; "Design of the First-in-Class, Highly Potent Irreversible Inhibitor Targeting the Menin-MLL Protein-Protein Interaction"; Angew. Chem. Int. Ed., 57; (2018); pp. 1601-1605.

(Continued)

*Primary Examiner* — John M Mauro
(74) *Attorney, Agent, or Firm* — Oblon, McClelland, Maier & Neustadt, L.L.P.

(57) ABSTRACT

The present invention relates to the compound of formula (I) wherein p is 1 or 2, $R^1$ is —$CF_3$ or the like, $R^{2a}$, $R^{2b}$, $R^{3a}$, and $R^{3b}$ are hydrogen atom or the like, X is —C(=O)— or the like, or a pharmaceutically acceptable salt thereof, which has an antitumor effect by inhibiting the binding between a MLL fusion protein that is infused with AF4, AF9, or the like, which is a representative fusion partner gene causing MLL leukemia, and menin.

(1)

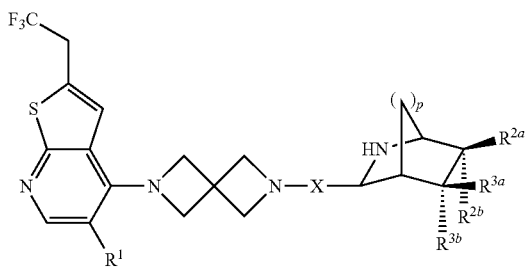

23 Claims, No Drawings

(56) References Cited

FOREIGN PATENT DOCUMENTS

| WO | WO 2017/207387 A1 | 12/2017 |
| WO | WO 2017/214367 A1 | 12/2017 |
| WO | WO 2018/024602 A1 | 2/2018 |
| WO | WO 2018/050684 A1 | 3/2018 |
| WO | WO 2018/050686 A1 | 3/2018 |
| WO | WO 2018/053267 A1 | 3/2018 |

OTHER PUBLICATIONS

International Preliminary Report on Patentability and Written Opinion of the International Searching Authority dated Oct. 6, 2020 in PCT/JP2019/013941, filed on Mar. 29, 2019; citing documents AN-AP on p. 1 of PTO 1449.

Imachi H., et al.; Menin, a product of the MENI gene, binds to estrogen receptor to enhance its activity in breast cancer cells: possibility of a novel predictive factor for tamoxifen resistance:; Breast Cancer Res Treat. 122; (2010); pp. 395-407.

Svoboda L.K., et al.; "Tumorigenicity of Ewing sarcoma is critically dependent on the trithorax proteins MLL1 and menin"; Oncotarget, vol. 8, No. 1; (2017); pp. 458-471.

Xu B., et al.; "Menin promotes hepatocellular carcinogenesis and epigenetically up-regulates Yap1 transcription"; Proc. Natl Acad. Sci. USA, vol. 110, No. 43; Oct. 22, 2013; pp. 17480-17485.

Zhu J., et al.; "Gain-of-function p53 mutants co-opt chromatin pathways to drive cancer growth"; Nature, vol. 525; Sep. 10, 2015; pp. 206-211.

International Search Report dated Jun. 25, 2019 in PCT/JP2019/013941, filed on Mar. 29, 2019, citing documents AN-AP.

Look A.T.; "Oncogenic Transcription Factors in the Human Acute Leukemias"; Science, vol. 278, Nov. 7, 1997; pp. 1059-1064.

Yokoyama A., et al.; "The Menin Tumor Suppressor Protein Is an Essential Oncogenic Cofactor for MLL-Associated Leukemogenesis"; Cell, vol. 123, Oct. 21, 2005; pp. 207-218.

Yokoyama A., et al.; "Menin Critically Links MLL Proteins with LEDGF on Cancer-Associated Target Genes"; Cancer Cell, 14; Jul. 2008; pp. 36-46.

Malik R., et al.; "Targeting the MLL complex in castration-resistance prostate cancer"; Nature Medicine, vol. 21, No. 4; Apr. 2015; pp. 344-352.

OPTICALLY ACTIVE CROSSLINKED CYCLIC SECONDARY AMINE DERIVATIVE

This application is a national stage application of PCT/JP2019/013941, filed Mar. 29, 2019, and claims priority to Japanese application 2018-067187, filed Mar. 30, 2018. The contents of both applications are incorporated herein by reference.

TECHNICAL FIELD

The present invention relates to an optically active bridged-cyclic secondary-amine derivative having a thienopyridine useful as a medicament, or a pharmaceutically acceptable salt thereof, and a pharmaceutical composition comprising it, or a medicament comprising the composition for treating pathology related to menin-MLL or preventing its relapse.

BACKGROUND ART

MLL leukemia is a disease that accounts for about 6 to 7% of acute myeloid leukemia (AML) and acute lymphoblastic leukemia (ALL), and about 1100 people are newly diagnosed with MLL leukemia each year in America. It has been reported that major fusion partner genes that cause MLL leukemia are likely to be AF9, ELL, ENL, AF10, and AF6 in AML, and AF4, ENL, and AF9 in ALL (Non-patent literature 1).

It is inferred that a MLL fusion protein fused with a fusion partner gene can cause unrestrained proliferation of undifferentiated hematopoietic cells to lead to leukemia (Non-patent literature 2). It has been reported that a MLL fusion protein firstly binds to menin to form a complex. Accordingly, it is expected that canceration caused by a MLL fusion protein can be prevented by inhibiting the first binding between a MLL fusion protein and menin (Non-patent literature 3).

It has been reported that MLL acts as an activation cofactor of an androgen signal in prostate cancer. Accordingly, it is expected that a small molecular inhibitor which is targeted to menin-MLL is useful as a medicament for treating the cancer (Non-patent literature 4).

It has been reported that menin acts as an activation cofactor of an estrogen signal in breast cancer. Accordingly, it is expected that a small molecular inhibitor which is targeted to menin-MLL is useful as a medicament of the cancer (Non-patent literature 5).

It has been reported that menin or MLL is important for tumor progression in Ewing's sarcoma, liver cancer, and p53 gain-of-function mutation cancer, and it is expected that a small molecular inhibitor which is targeted to menin-MLL is useful as a medicament of the cancers (Non-patent literatures 6, 7, 8).

Patent literatures 1 to 16 and Non-patent literatures 9 to 12 disclose small molecular inhibitors which are targeted to menin-MLL. The present compound of the following formula (1) which is an optically active bridged cyclic secondary-amine derivative having a thienopyridine, however, is not disclosed or suggested in them.

PRIOR ART

Patent Reference

[Patent Literature 1] WO2011/029054
[Patent Literature 2] WO2014/164543
[Patent Literature 3] US2014/0371239 A
[Patent Literature 4] WO2016/040330
[Patent Literature 5] WO2016/195776
[Patent Literature 6] WO2016/197027
[Patent Literature 7] WO2017/161002
[Patent Literature 8] WO2017/161028
[Patent Literature 9] WO2017/112768
[Patent Literature 10] WO2017/207387
[Patent Literature 11] WO2017/192543
[Patent Literature 12] WO2017/214367
[Patent Literature 13] WO2018/024602
[Patent Literature 14] WO2018/050684
[Patent Literature 15] WO2018/050686
[Patent Literature 16] WO2018/053267

Non-patent Reference

[Non-patent Literature 1] Look A. T, Science, 278 (5340): 1059-1064 (1997)
[Non-patent Literature 2] Yokoyama A, et al., Cell 123 (2): 207-218 (2005)
[Non-patent Literature 3] Yokoyama, A et al., Cancer Cell. 14(1): 36-46 (2008)
[Non-patent Literature 4] Malik, R. et al., Nature Medicine. 21(4):344-352 (2015)
[Non-patent Literature 5] Imachi, H et al., Breast Cancer Res Treat. 122(2):395-407 (2010)
[Non-patent Literature 6] Svoboda, L. K. et al., Oncotargrt. 8(1):458-471 (2017)
[Non-patent Literature 7] Xu, B._et al., Proc Natl Acad Sci USA. 110(43): 17480-17485 (2013)
[Non-patent Literature 8] Zhu, J. et al., Nature. 525 (7568): 206-211 (2015)
[Non-patent Literature 9] Grembecka, J. et al., Nature Chemical Biology. 8: 277-284 (2012)
[Non-patent Literature 10] Borkin, D. et al., Cancer Cell. 27 589-602 (2015) [Non-patent Literature II] Borkin, D. et al., J. Med. Chem. 59: 892-913 (2016)
[Non-patent Literature 12] Xu, S. et al., Angew. Chem. Int. Ed. 57: 1601-1605 (2018)

SUMMARY OF INVENTION

Technical Problem

The purpose of the present invention may be to provide a compound which has an antitumor effect by inhibiting the binding between a MLL fusion protein that is fused with AF4, AF9, etc., which is a representative fusion partner gene causing MLL leukemia, and menin. More preferably, the purpose of the present invention may be to provide a compound which has an antitumor effect by inhibiting the menin-MLL binding, and also has a good pharmacokinetic character. In other words, the purpose of the present invention is to provide an antitumor medicament with high therapeutic effect.

Solution to Problem

The present inventors have extensively studied to reach the above purpose, and then have found that a compound of the following formula (1) or a pharmaceutically acceptable salt thereof (hereinafter, it may be referred to as "the present compound") has an excellent antitumor effect through a potent inhibitory effect on the menin-MLL binding. Based upon the findings, the present invention has been achieved.

Accordingly, the present invention is described as follows:

(Item 1)

A compound of formula (1):

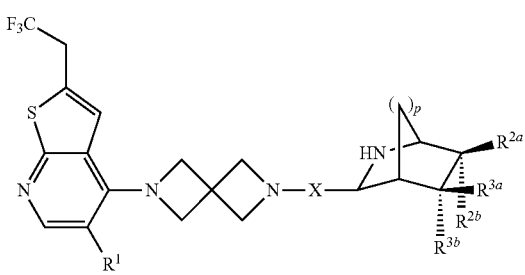

(1)

or a pharmaceutically acceptable salt thereof, wherein
p is 1 or 2,
$R^1$ is —$CF_3$, —$CHF_2$, or cyano,
$R^{2a}$, $R^{2b}$, $R^{3a}$, and $R^{3b}$ are each independently hydrogen atom, halogen atom, $C_{1-6}$ alkyl, $C_{2-6}$ alkenyl, $C_{2-6}$ alkynyl, $C_{3-10}$ cycloalkyl, —$OR^4$, 3- to 10-membered saturated heterocyclyl, $C_{6-10}$ aryl, or 5- to 12-membered heteroaryl. (wherein the alkyl may be substituted with 1-3 fluorine atoms; the cycloalkyl and the saturated heterocyclyl are each independently substituted with the same or different 1-5 substituents selected from the group consisting of fluorine atom and $C_{1-3}$ alkyl; and the aryl and the heteroaryl are each independently substituted with the same or different 1-5 substituents selected from the group consisting of fluorine atom, chlorine atom, bromine atom, and $C_{1-3}$ alkyl); or $R^{2a}$ and $R^{2b}$ may be combined together to form =O, and $R^{3a}$ and $R^{3b}$ may be combined together to form =O,
$R^4$ is, each independently if there are plural, hydrogen atom, $C_{1-6}$ alkyl, $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl (wherein the alkyl may be substituted with the same or different 1-5 substituents selected from the group consisting of $C_{3-10}$ cycloalkyl, 3- to 10-membered saturated heterocyclyl, $C_{6-10}$ aryl, and 5- to 12-membered heteroaryl; the cycloalkyl and the saturated heterocyclyl may be each independently substituted with the same or different 1-5 substituents selected from the group consisting of fluorine atom and $C_{1-3}$ alkyl; and the aryl and the heteroaryl may be each independently substituted with the same or different 1-5 substituents selected from the group consisting of fluorine atom, chlorine atom, bromine atom, and $C_{1-3}$ alkyl), and
X is —C(=O)— or $C_{1-6}$ alkylene.

(Item 2)

The compound of Item 1 or a pharmaceutically acceptable salt thereof, wherein X is —C(=O)—, and $R^1$ is —$CF_3$.

(Item 3)

The compound of Item 1 or 2 or a pharmaceutically acceptable salt thereof, wherein
$R^{2a}$, $R^{2b}$, $R^{3a}$, and $R^{3b}$ are each independently hydrogen atom, fluorine atom, $C_{1-6}$ alkyl, or —$OR^4$; or $R^{2a}$ and $R^{2b}$ may be combined together to form =O, and $R^{3a}$ and $R^{3b}$ may be combined together to form =O, and
$R^4$ is, each independently if there are plural, hydrogen atom, $C_{2-6}$ alkenyl, or $C_{1-6}$ alkyl (wherein the alkyl may be substituted with $C_{6-10}$ aryl).

(Item 4)

The compound of Item 1 or a pharmaceutically acceptable salt thereof, wherein formula (1) is the following formula (1-A):

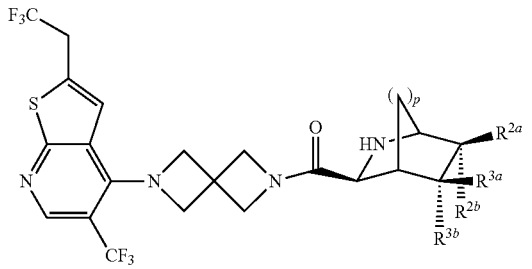

(1-A)

wherein
p is 1 or 2,
$R^{2a}$ and $R^{2b}$ are each independently hydrogen atom, fluorine atom, or —$OR^4$,
$R^{3a}$ and $R^{3b}$ are each independently hydrogen atom or fluorine atom, or $R^{3a}$ and $R^{3b}$ may be combined together to form =O, and
$R^4$ is, each independently if there are plural, hydrogen atom, $C_{2-4}$ alkenyl, or $C_{1-3}$ alkyl (wherein the alkyl may be substituted with phenyl).

(Item 5)

The compound of any one of Items 1 to 4 or a pharmaceutically acceptable salt thereof, wherein
$R^{2a}$ and $R^{2b}$ are hydrogen atom, and
$R^{3a}$ and $R^{3b}$ are each independently hydrogen atom or fluorine atom.

(Item 6)

The compound of any one of Items 1 to 5 or a pharmaceutically acceptable salt thereof, wherein $R^{3a}$ is hydrogen atom, and $R^{3b}$ is fluorine atom.

(Item 7)

The compound of Item 1 or a pharmaceutically acceptable salt thereof, wherein the compound is selected from the following:
{(1S,3S,4S,5S)-5-fluoro-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone (Example 1),
[(1R,3S,4S)-2-azabicyclo[2.2.1]heptan-3-yl]{6-[2-(2,2,2-trifluoroethyl)-5-(trifluoromethyl)thieno[2,3-b)pyridin-4-yl]-2,6-diazaspiro[3.3]heptan-2-yl}methanone (Example 2),
[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 3),
[(1S,3S,4S)-5,5-difluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 4),
[(1S,3S,4R,6S)-6-hydroxy-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 6),
(1S,3S,4S)-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octan-5-one (Example 8),
[(1S,3S,4S,5S)-5-fluoro-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 9),

[(1S,3S,4R,6R)-6-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 10), {(1S,3S,4R,6S)-6-[(prop-2-en-1-yl)oxy]-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone (Example 11),

[(1S,3S,4R,6S)-6-(benzyloxy)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 13), 4-{6-[(3S)-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 20), 4-{6-[(1R,3S,4S)-2-azabicyclo[2.2.1]heptane-3-carbonyl]-2,6-diazaspiro[3.3]heptan-2-yl}-2-(2,2,2-trifluoroethyl)thieno[2,3-b]pyridine-5-carbonitrile (Example 21), 4-{6-[(1S,3S,4S,5S)-5-fluoro-2-azabicyclo[2.2.2]octane-3-carbonyl]-2,6-diazaspiro[3.3]heptan-2-y}-2-(2,2,2-trifluoroethyl)thieno[2,3-b]pyridine-5-carbonitrile (Example 22), 4-{6-[(1S,3S,4S)-5,5-difluoro-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 23), 4-{6-[(1S,3S,4S)-5-oxo-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile (Example 25),

[(3S)-2-azabicyclo[2.2.2]octan-3-yl]{6-[5-(difluoromethyl)-2-(2,2,2-trifluoroethyl)thieno[2,3-b]pyridin-4-yl]-2,6-diazaspiro[3.3]heptan-2-yl}methanone (Example 26), and

[(1R,3S,4S)-2-azabicyclo[2.2.1]heptan-3-yl]{6-[5-(difluoromethyl)-2-(2,2,2-trifluoroethyl)thieno[2,3-b]pyridin-4-yl]-2,6-diazaspiro[3.3]heptan-2-yl}methanone (Example 27).

(Item 8)

The compound of Item 1 or a pharmaceutically acceptable salt thereof, wherein the compound is selected from the following:

{(1S,3S,4S,5S)-5-fluoro-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone (Example 1),

[(1R,3S,4S)-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 2),

[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 3),

[(1S,3S,4S)-5,5-difluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 4),

[(1S,3S,4R,6S)-6-hydroxy-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 6), (1S,3S,4S)-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octan-5-one (Example 8),

[(1S,3S,4S,5S)-5-fluoro-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 9),

[(1S,3S,4R,6R)-6-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 10), {(1S,3S,4R,6S)-6-[(prop-2-en-1-yl)oxy]-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone (Example 11), and

[(1S,3S,4R,6S)-6-(benzyloxy)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 13).

(Item 9)

The compound of Item 1 or a pharmaceutically acceptable salt thereof, wherein the compound is selected from the following:

{(1S,3S,4S,5S)-5-fluoro-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone (Example 1),

[(1R,3S,4S)-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 2),

[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 3), and

[(1S,3S,4S,5S)-5-fluoro-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 9).

(Item 10)

The compound of Item 1 or a pharmaceutically acceptable salt thereof, wherein the compound is the following:

{(1S,3S,4S,5S)-5-fluoro-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone (Example 1).

(Item 11)

The compound of Item 1 or a pharmaceutically acceptable salt thereof, wherein the compound is the following:

[(1R,3S,4S)-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 2).

(Item 12)

The compound of Item 1 or a pharmaceutically acceptable salt thereof, wherein the compound is the following:

[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 3).

(Item 13)

The compound of Item 1 or a pharmaceutically acceptable salt thereof, wherein the compound is the following:

[(1S,3S,4S,5S)-5-fluoro-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone (Example 9).

(Item 14)

A pharmaceutical composition comprising the compound of any one of Items 1 to 13 or a pharmaceutically acceptable salt thereof.

(Item 15)

An antitumor medicament comprising the compound of any one of Items 1 to 13 or a pharmaceutically acceptable salt thereof.

(Item 16)

The antitumor medicament of Item 15, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

(Item 17)

The antitumor medicament of Item 15 or 16, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic myeloid leukemia, malignant lymphoma (including B-cell lymphoma), myeloma (including multiple myeloma), brain tumor, prostate cancer, breast cancer, neuroblastoma, Ewing's sarcoma, or liver cancer.

(Item 18)

The antitumor medicament of any one of Items 15 to 17, wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, multiple myeloma, neuroblastoma, or prostate cancer.

(Item 19)

The antitumor medicament of any one of Items 15 to 18, wherein the tumor is MLL acute leukemia, or NPM mutated acute leukemia.

(Item 20)

The antitumor medicament of any one of Items 15 to 19, wherein the tumor is accompanied by high expression of HOXa gene cluster, or MEIS gene cluster.

(Item 21)

The antitumor medicament of any one of Items 15 to 20, wherein the tumor is accompanied by p53 gain-of-function mutation.

(Item 22)

A method for treating a tumor comprising administrating the compound of any one of Items 1 to 13 or a pharmaceutically acceptable salt thereof to a patient in need thereof.

(Item 23)

The method of Item 22, wherein the tumor is involved in Menin-MLL.

(Item 24)

Use of the compound of any one of Items 1 to 13 or a pharmaceutically acceptable salt thereof in the manufacture of an antitumor medicament.

(Item 25)

The compound of any one of Items 1 to 13 or a pharmaceutically acceptable salt thereof for use in the treatment of a tumor.

(Item 26)

A pharmaceutical composition comprising the compound of any one of Items 1 to 13 or a pharmaceutically acceptable salt thereof in combination with at least one different agent or a pharmaceutically acceptable salt thereof, wherein the different agent is selected from the group consisting of an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other anticancer medicaments.

(Item 27)

The compound of any one of Items 1 to 13 or a pharmaceutically acceptable salt thereof for treating a tumor, which is used in combination with at least one different agent or a pharmaceutically acceptable salt thereof, wherein the different agent is selected from an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, an biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicaments.

Effect of the Invention

The present invention provides an inhibitor of the binding between menin and MLL fusion protein, comprising an optically-active bridged-cyclic secondary-amine derivative or a pharmaceutically acceptable salt thereof. The compound of the present invention is useful as a medicament for diseases involved in the binding between menin and MLL, and is applicable to a patient suffering from, specifically, MLL acute leukemia, NPM mutated acute leukemia, prostate cancer, breast cancer, Ewing's sarcoma, liver cancer, p53 gain-of-function mutated cancer, and the like.

DESCRIPTION OF EMBODIMENTS

Hereinafter, terms used herein are explained as follows.

The "halogen atom" includes, for example, fluorine atom, chlorine atom, bromine atom, and iodine atom, and the like. It is preferably fluorine atom. Fluorine atom, chlorine atom, bromine atom, or iodine atom which are used as a substituent means fluoro group, chloro group, bromo group, or iodo group, respectively.

The "$C_{1-6}$ alkyl" means alkyl having 1 to 6 carbon atoms, and "$C_6$ alkyl" means alkyl having 6 carbon atoms. The same is applied to the case of the other carbon numbers.

The "$C_{1-6}$ alkyl" means straight or branched chain saturated hydrocarbon group having 1 to 6 carbon atoms. The $C_{1-6}$, alkyl includes preferably "$C_{1-4}$ alkyl", more preferably "$C_{1-3}$alkyl". The "$C_{1-3}$ alkyl" includes, for example, methyl, ethyl, propyl, 1-methylethyl, and the like. The "$C_{1-4}$ alkyl" includes, for example, butyl, 1,1-dimethylethyl, 1-methylpropyl, 2-methylpropyl, and the like, besides the examples listed in the said "$C_{1-3}$ alkyl". The "$C_{1-6}$ alkyl" includes, for example, pentyl, 1,1-dimethylpropyl, 1,2-dimethylpropyl, 1-methylbutyl, 2-methylbutyl, 4-methylpentyl, 3-methylpentyl, 2-methylpentyl, 1-methylpentyl, hexyl, and the like, besides the examples listed in the said "$C_{1-4}$ alkyl".

The "$C_{2-6}$ alkenyl" means straight or branched chain unsaturated hydrocarbon group having 2 to 6 carbon atoms and 1 to 3 double bonds. The "$C_{2-6}$ alkenyl" includes preferably "$C_{2-4}$ alkenyl". The "$C_{2-4}$ alkenyl" includes, for example, vinyl, propenyl, methylpropenyl, butenyl, and the like. The "$C_{2-6}$ alkenyl" includes, for example, pentenyl, hexenyl, and the like, besides the examples listed in the said "$C_{2-4}$ alkenyl".

The "$C_{2-6}$ alkynyl" means straight or branched chain unsaturated hydrocarbon group having 2 to 6 carbon atoms and a triple bond. The "$C_{2-6}$ alkynyl" includes preferably "$C_{1-4}$ alkynyl". The "$C_{2-4}$ alkynyl" includes, for example, propynyl, methylpropynyl, butynyl, and the like. The "$C_{2-6}$ alkynyl" includes, for example, methylbutynyl, pentynyl, hexynyl, and the like, besides the examples listed in the said "$C_{2-4}$ alkynyl".

The "$C_{1-6}$ alkylene" means divalent straight or branched chain saturated hydrocarbon group having 1 to 6 carbon atoms. The "$C_{1-6}$ alkylene" includes preferably "$C_{1-3}$ alkylene". The "$C_{1-3}$ alkylene" includes, for example, methylene, ethylene, propylene, 1-methylethylene, and the like.

The "$C_{3-10}$ cycloalkyl" means cyclic saturated hydrocarbon group having 3 to 10 carbon atoms, which may have a partially-unsaturated bond or a bridged structure. The "$C_{3-10}$ cycloalkyl" includes preferably "$C_{3-7}$ cycloalkyl". The "$C_{3-7}$ cycloalkyl" includes, for example, cyclopropyl, cyclobutyl, cyclopentyl, cyclohexyl, cycloheptyl, and the like. The "$C_{3-10}$ cycloalkyl" includes, for example, cycloheptyl, cyclooctyl, cyclononyl, cyclodecyl, adamantyl, and the like, besides the examples listed in the said "$C_{3-7}$ cycloalkyl".

The "$C_{3-10}$ cycloalkyl" also encompasses a fused ring with an aromatic hydrocarbon ring. The fused ring compounds includes, for example, the following structures:

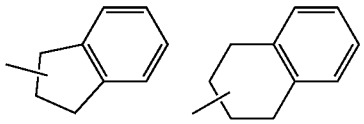

The "3- to 10-membered saturated heterocyclyl" means a saturated heterocycle composed of 3 to 10 atoms including 1 to 2 atoms selected independently from the group consisting of nitrogen atom, oxygen atom and sulfur atom, besides carbon atoms, which may have a partially-unsaturated bond and a bridged structure. The "3- to 10-membered saturated heterocyclyl" is preferably "4- to 7-membered monocyclic saturated heterocyclyl", more preferably "5- or 6-membered monocyclic saturated heterocyclyl". The "5- or 6-membered monocyclic saturated heterocyclyl" includes, for example, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, oxoimidazolidinyl, dioxoimidazolidinyl, oxooxazolidinyl, dioxooxazolidinyl, dioxothiazolidinyl, tetrahydrofuranyl, tetrahydropyranyl, and the like. The "4- to 7-membered monocyclic saturated heterocyclyl" includes, for example, oxetanyl, azetidinyl, and the like, besides the examples listed in the said "5- or 6-membered monocyclic saturated heterocyclyl". The "3- to 10-membered saturated heterocyclyl" includes, for example, epoxy, aziridinyl, and the like, besides the examples listed in the said "4- to 7-membered monocyclic saturated heterocyclyl".

The "3- to 10-membered saturated heterocyclyl" also encompasses bicyclic compounds, i.e., "3- to 10-membered saturated heterocyclyl" fused with a 6-membered aromatic hydrocarbon ring or a 6-membered aromatic heterocycle. The 6-membered aromatic hydrocarbon ring in the fused ring includes benzene ring and the like. The 6-membered aromatic heterocycle in the fused ring includes pyridine, pyrimidine, pyridazine, pyrazine, and the like. The bicyclic "3- to 10-membered saturated heterocyclyl" which is a fused bicyclyl includes dihydroindolyl, dihydroisoindolyl, dihydropurinyl, dihydrothiazolopyrimidinyl, dihydrobenzodioxanyl, isoindolyl, indazolyl, tetrahydroquinolinyl, tetrahydroisoquinolinyl, tetrahydronaphthyridinyl, and the like.

The "$C_{6-10}$ aryl" means aromatic hydrocarbon ring having 6 to 10 carbon atoms. The "$C_{6-10}$ aryl" includes, for example, phenyl, 1-naphthyl, 2-naphthyl, and the like. It includes preferably phenyl.

The "$C_{6-10}$ aryl" also encompasses bicyclic compounds, i.e., $C_{6-10}$ aryl fused with $C_{4-E}$ cycloalkyl or 5- or 6-membered saturated heterocycle. The bicyclic "$C_{6-10}$ aryl" which is a fused bicyclyl includes, for example, the following groups:

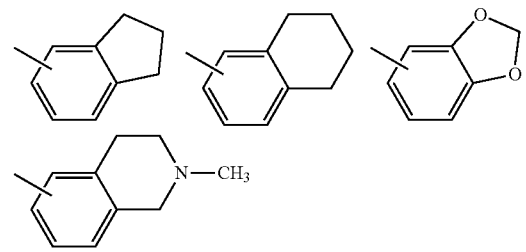

The "aromatic hydrocarbon ring" means a cyclic part of the said "$C_{6-10}$ aryl".

The "5- to 12-membered heteroaryl" means monocyclic 5-to 7-membered aromatic heterocyclyl or bicyclic 8- to 12-membered aromatic heterocyclyl having 1 to 4 atoms selected independently from the group consisting of nitrogen atom, oxygen atom and sulfur atom. It is preferably "5- to 7-membered monocyclic heteroaryl". It is more preferably pyridyl, pyrimidinyl, quinolyl, or isoquinolyl. It is even more preferably pyridyl. The "5- to 7-membered monocyclic heteroaryl" includes, for example, pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, oxadiazolyl, triazolyl, tetrazolyl, and the like. The "5- to 12-membered heteroaryl" includes indolyl, indazolyl, chromenyl, quinolyl, isoquinolyl, benzofuranyl, benzothienyl, benzooxazolyl, benzothiazolyl, benzoisoxazolyl, benzoisothiazolyl, benzotriazolyl, benzoimidazolyl, and the like, besides the examples listed in the said "5- to 7-membered monocyclic heteroaryl".

The "aromatic heterocyclyl" means a cyclic part of the said "5- to 12-membered heteroaryl".

The "cancer" and "tumor" are used interchangeably, and the both mean malignant neoplasm, which encompasses carcinoma, sarcoma, and hematologic malignancy. The "cancer" and "tumor" include, for example, acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, skin cancer, and the like. The above tumors may be accompanied by increased expression or mutation of specific genes. The tumors accompanied by increased expression of genes include, for example, tumors accompanied by high expression of HOXa gene cluster, tumors accompanied by high expression of MEIS gene cluster, and the like. The tumors accompanied by mutation of genes include tumors accompanied by p53 gain-of-function mutation and the like.

The "antitumor medicament" used herein includes a medicament having antitumor activity, and a medicament for preventing relapse. An antitumor medicament may be used to kill tumor cells, suppress tumor cell growth, or inhibit tumor metastasis and relapse. The medicament for the treatment means a medicament used for treating a patient affected with tumor, and the medicament for preventing the relapse means a medicament used for preventing tumor relapse of a patient who ameliorated tumor.

In the present compound of formula (1), preferred p, $R^1$, $R^{2a}$, $R^{2b}$, $R^{3a}$, $R^{3b}$, $R^4$, and X are as follows, but the technical scope of the present invention is not limited to the scope of compounds listed below.

In an embodiment, p includes 1. In another embodiment, p includes 2.

$R^1$ is preferably —$CF_3$.

$R^{2a}$ includes preferably hydrogen atom, fluorine atom, $C_{1-6}$ alkyl, and —$OR^4$, more preferably hydrogen atom, fluorine atom, and —$OR^4$. It is even more preferably hydrogen atom.

$R^{2b}$ includes preferably hydrogen atom, fluorine atom, $C_{1-6}$ alkyl, and —$OR^4$, more preferably hydrogen atom, fluorine atom, and —$OR^4$. It is even more preferably hydrogen atom.

$R^{3a}$ includes preferably hydrogen atom and fluorine atom, or preferably $R^{3a}$ and $R^{3b}$ are combined together to form =O. It is more preferably hydrogen atom or fluorine atom, even more preferably hydrogen atom.

$R^{3b}$ includes preferably hydrogen atom and fluorine atom, or preferably $R^{3a}$ and $R^{3b}$ are combined together to form =O. It is more preferably hydrogen atom or fluorine atom, even more preferably fluorine atom.

$R^4$ includes preferably hydrogen atom, $C_{1-6}$ alkyl which may be substituted with $C_{6-10}$ aryl, and $C_{2-6}$ alkenyl. More preferably, it includes hydrogen atom, $C_{1-3}$ alkyl which may be substituted with phenyl, and $C_{2-4}$ alkenyl. It is even more preferably allyl or benzyl. As an embodiment, $R^4$ includes allyl. As another embodiment, it includes benzyl.

X is preferably —C(=O)-.

In the present compound of formula (1-A), preferred p, $R^{2a}$, $R^{2b}$, $R^{3a}$, $R^{3b}$, and $R^4$ are as follows, but the technical scope of the present invention is not limited to the scope of compounds listed below.

In an embodiment, p includes 1. In another embodiment, p includes 2.

$R^{2a}$ includes preferably hydrogen atom and fluorine atom, more preferably hydrogen atom.

$R^{2b}$ includes preferably hydrogen atom and fluorine atom, more preferably hydrogen atom.

$R^{3a}$ includes preferably hydrogen atom and fluorine atom, more preferably hydrogen atom. As an embodiment, $R^{3a}$ includes hydrogen atom. As another embodiment, it includes fluorine atom.

$R^{3b}$ includes preferably hydrogen atom and fluorine atom, more preferably fluorine atom. As an embodiment, $R^{3b}$ includes hydrogen atom. As another embodiment, it includes fluorine atom.

$R^4$ includes preferably hydrogen atom, $C_{1-3}$ alkyl which may be substituted with phenyl, and $C_{2-4}$ alkenyl. More preferably, it includes ally and benzyl. As an embodiment, $R^4$ includes allyl. As another embodiment, it includes benzyl.

In an embodiment of $R^{2a}$, $R^{2b}$, $R^{3a}$, and $R^{3b}$, all of $R^{2a}$, $R^{2b}$, and $R^{3a}$ are hydrogen atom, and $R^{3b}$ is fluorine atom. In another embodiment thereof, all of $R^{2a}$, $R^{2b}$, and $R^{3b}$ are hydrogen atom, and $R^{3a}$ is fluorine atom. Further in another embodiment thereof, both of $R^{2a}$ and $R^{2b}$ are hydrogen atom, and both of $R^{3a}$ and $R^{3b}$ are fluorine atom.

In an embodiment, the present compound of formula (1) includes the following (A):

(A)

A Compound or pharmaceutically acceptable salt thereof, wherein p is 1 or 2, $R^1$ is —$CF_3$, $R^{2a}$ and $R^{2b}$ are each independently hydrogen atom, fluorine atom, or —$OR^4$, $R^{3a}$ and $R^{3b}$ are each independently hydrogen atom or fluorine atom; or $R^{3a}$ and $R^{3b}$ may be combined together to form =O, $R^4$ is, each independently if there are plural, hydrogen atom, $C_{2-4}$ alkenyl, or $C_{1-3}$ alkyl which may be substituted with phenyl, and X is —C(=O)—.

An embodiment of the present compound of formula (1) includes the following (B):

(B)

A Compound or pharmaceutically acceptable salt thereof, wherein p is 1 or 2, $R^1$ is —$CF_3$, $R^{2a}$ and $R^{2b}$ are each independently hydrogen atom, fluorine atom, or —$OR^4$, $R^{3a}$ and $R^{3b}$ are each independently hydrogen atom or fluorine atom; or $R^{3a}$ and $R^{3b}$ may be combined together to form =O, $R^4$ is, each independently if there are plural, allyl or benzyl, and X is —C(=O)—.

An embodiment of the present compound of formula (1) includes the following (C):

(C)

A compound or pharmaceutically acceptable salt thereof, wherein p is 1 or 2, $R^1$ is —$CF_3$, $R^{2a}$ and $R^{2b}$ are hydrogen atom, $R^{3a}$ and $R^{3b}$ are each independently hydrogen atom or fluorine atom, and X is —C(=O)—.

Hereinafter, the processes to prepare the compound of the present invention of formula (1) are exemplified along with examples, but the processes to prepare the compound of the present invention should not be limited to the examples.

Compounds used in the following process may exist as their salts unless they affect reactions.

The compound of the present invention can be prepared from known compounds as starting materials, for example, by the methods shown below, or similar methods thereto, or optionally in combination with synthetic methods well-known to a person skilled in the art.

Preparation Process 1

The compound of the present invention of formula (1) can be prepared, for example, by the following process:

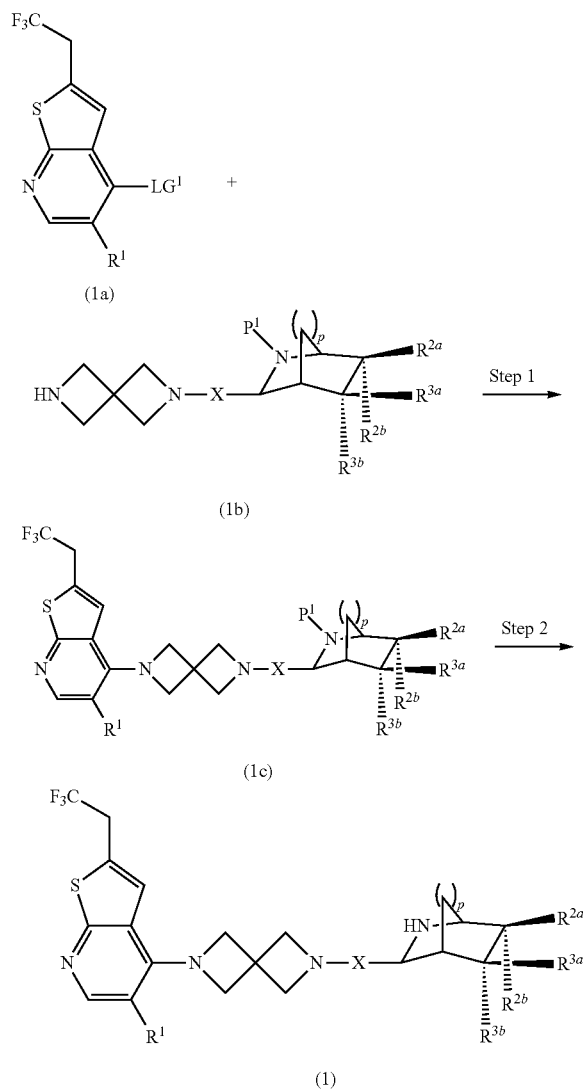

wherein p, $R^1$, $R^{2a}$, $R^{2b}$, $R^{3a}$, $R^{3b}$, and X are as defined in Item 1, $LG^1$ is a leaving group, and $P^1$ is an amino-protecting group, wherein $LG^1$ includes, for example, halogen atom, methanesulfonyloxy, p-toluenesulfonyloxy, trifluoromethanesulfonyloxy, phenoxy, trifluorophenoxy, tetrafluorophenoxy, pentafluorophenoxy, nitrophenoxy, and the like; P: includes, for example, amino-protecting groups described in Protective Groups in Organic Synthesis (edited by Theodora W. Greene, Peter G. M. Wuts, issued by John Wiley & Sons, Inc. in 1999), and the like.

(Step 1)

Compound (1c) can be prepared by reacting compound (1a) obtained in the following process with compound (1b) obtained in the following procedure in the presence or absence of an appropriate base in an appropriate solvent.

Compound (1b) used herein can be obtained by the following Preparation Process 3 (as compound (3d)), or by the following Preparation Process 4 (as compound (4c)).

The base used herein includes, for example, organic bases such as triethylamine, diisopropylethylamine, tributylamine, 1,5-diazabicyclo[4.3.0]non-5-ene (DBN), 1,8-diazabicyclo[5.4.0]undec-7-ene (DBU), pyridine, dimethylaminopyridine, picoline, and N-methylmorpholine (NMM); and inorganic bases such as sodium bicarbonate, potassium bicarbonate, sodium carbonate, potassium carbonate, sodium hydroxide, and potassium hydroxide. The base includes preferably triethylamine, diisopropylethylamine, and the like.

The solvent used herein includes, for example, ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethylsulfoxide; and mixtures thereof, but not specifically limited thereto unless it reacts under the reaction condition in the present processes. The solvent includes preferably tetrahydrofuran, toluene, N,N-dimethylformamide, and the like.

The reaction temperature is generally −80° C. to reflux temperature, preferably 25° C. to 90° C.

The reaction time is generally 30 minutes to 48 hours, preferably 6 to 12 hours.

Alternatively, compound (1a) may be coupled with compound (1b) in the presence of an appropriate metal catalyst in an appropriate solvent. The reaction condition includes, for example, Ulmann-type condition (for example, heating under reflux with a metal catalyst such as copper(II) acetate in an aprotic solvent such as DMF), Buchwald-type condition (for example, heating under reflux with alkali metal carbonate such as cesium carbonate; BINAP; a palladium catalyst such as $Pd_2(dba)_3$ and $Pd(OAc)_2$; and a ligand such as dppf and Xantphos, in an inert solvent under the reaction conditions such as toluene), and the like.

The solvent used herein includes, for example, alcohol solvents such as methanol, ethanol, 2-propanol (isopropyl alcohol), and tert-butanol; ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethylsulfoxide; water; and mixtures thereof, but should not specifically limited thereto unless it reacts under the reaction condition in the present processes. The solvent includes preferably totrahydrofuran, toluene, N,N-dimethylformamide, and the like.

The reaction temperature is generally −80° C. to reflux temperature, preferably 25° C. to 90° C.

The reaction time is generally 30 minutes to 48 hours, preferably 6 to 12 hours.

(Step 2)

Compound (1) can be prepared by removing protecting group $P^1$ from compound (1c). The present step can be carried out according to a method described, for example, in Protective Groups in Organic Synthesis (edited by Theodora W. Greene, Peter G. M. Wuts, issued by John Wiley & Sons, Inc. in 1999), and the like.

Preparation Process 2

The compound of formula (1a) can be prepared, for example, by the following process:

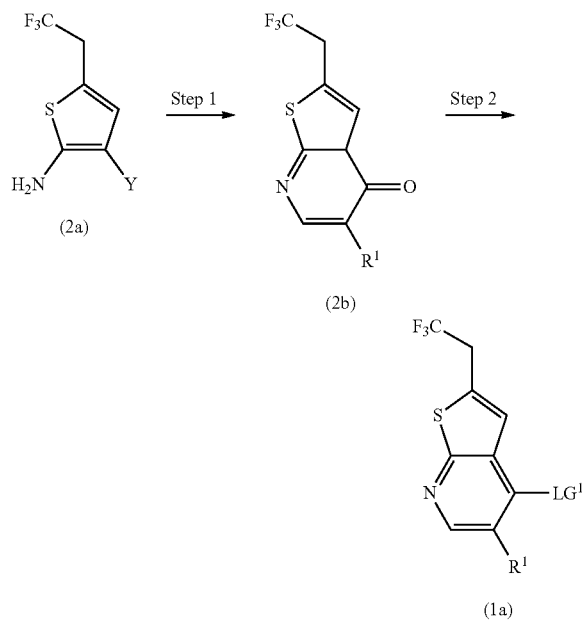

wherein Y is hydrogen atom, an ester, etc., $R^1$ is as defined in Item 1, and $LG^1$ is as defined in Preparation Process 1.

Compound (2a) can be prepared by a method described in WO 2014/164543 or a similar method thereto.

(Step 1)

Compound (2b) can be prepared from compound (2a) by a method described in Tetrahedron Letters, 49(48): 6850-6852 (2008), J. Med. Chem., 48(18): 5794-5804 (2005), Journal of Heterocyclic Chemistry, 28(8): 1953-1955 (2991), etc. or a similar method thereto.

(Step 2)

Compound (1a) can be prepared from compound (2b) by a method described in Comprehensive Organic Transformation $2^{nd}$ Edition (edited by Larock R. C., issued by John Wiley & Sons, Inc., in 1989), etc. or a similar method thereto.

Preparation Process 3

The compound of formula (3d) can be prepared, for example, by the following process:

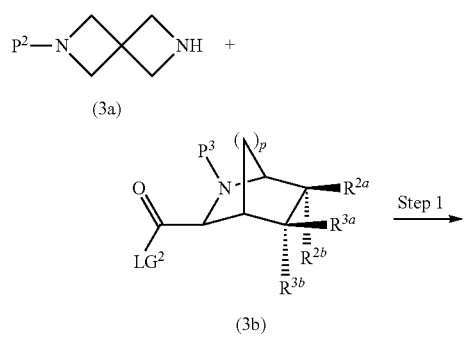

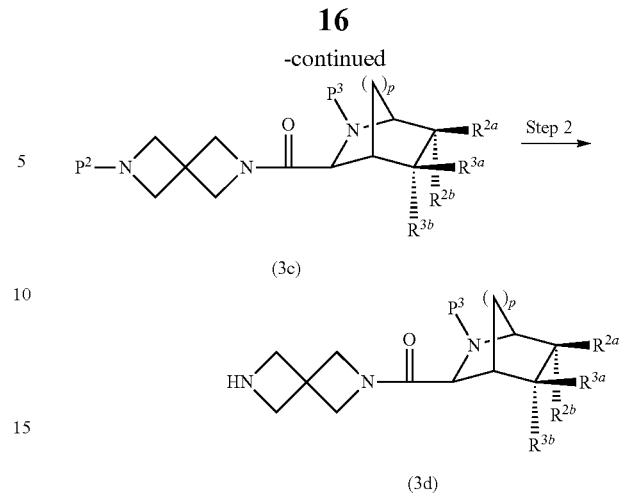

wherein p, $R^{2a}$, $R^{2b}$, $R^{3a}$, and $R^{3b}$ are as defined in Item 1, $LG^2$ is a leaving group, $P^2$ and $P^3$ are amino-protecting groups, wherein $LG^2$ includes, for example, halogen atom, hydroxy, and the like; and $P^2$ and $P^3$ include, for example, amino-protecting groups described in Protective Groups in Organic Synthesis (edited by Theodora W. Greene, Peter G. M. Wuts, issue by John Wiley & Sons, Inc. in 1999), and the like.

Compound (3a) can be prepared by a method described in Organic Letters, 2008, 10(16), 3525-3526, etc. or a similar method thereto, or can be obtained as a marketed product.

Compound (3b) can be prepared by a method described in JP 2007-510619 A, Comprehensive Organic Transformation $2^{nd}$ Edition (edited by Larock R. C., issued by John Wiley & Sons, Inc., in 1989), etc. or a similar method thereto, or can be obtained as a marketed product.

(Step 1)

Compound (3c) can be prepared by reacting compound (3a) with compound (3b) such as carboxylic acid compound and acid chloride compound in the presence or absence of an appropriate condensing agent and/or an appropriate base in an appropriate solvent.

The base used herein includes aminos such as triethylamine, diisopropylethylamine, and pyridine; and carbonates of alkali metal such as potassium carbonate, sodium carbonate, and sodium bicarbonate. The base includes preferably triethylamine, diisopropylethylamine, and pyridine.

The condensing agent used herein is optionally selected from condensing agents commonly-used in organic synthetic chemistry, and includes preferably 1-ethyl-3-(3-dimethylaminopropyl)carbodiimide hydrochloride, 1-hydroxybenzotriazole, and the like.

The solvent used herein includes, for example, ether solvents such as diethyl ether, diisopropyl ether, tetrahydrofuran, methylcyclopentyl ether, anisole, and 1,4-dioxane; aromatic hydrocarbon solvents such as benzene, toluene, chlorobenzene, and xylene; ester solvents such as ethyl acetate and methyl acetate; aprotic solvents such as N,N-dimethylformamide, N,N-dimethylacetamide, N-methyl-2-pyrrolidinone, 1,3-dimethyl-2-imidazolidinone, and dimethylsulfoxide; and mixtures thereof, but not specifically limited thereto unless it reacts under the reaction condition in the present processes. The solvent includes preferably tetrahydrofuran, toluene, N,N-dimethylformamide, and the like.

The reaction time is generally 5 minutes to 72 hours, preferably 30 minutes to 24 hours.

The reaction temperature is generally −78° C. to 200° C., preferably −78° C. to 80° C.

(Step 2)

Compound (3d) can be prepared by removing protecting group P² from compound (3c). The present step can be carried out, for example, according to a method described in Protective Groups in Organic Synthesis (edited by Theodora W. Greene, Peter G. M. Wuts, issued by John Wiley & Sons, Inc. in 1999), and the like.

Preparation Process 4

The compound of formula (4c) can be prepared, for example, by the following process:

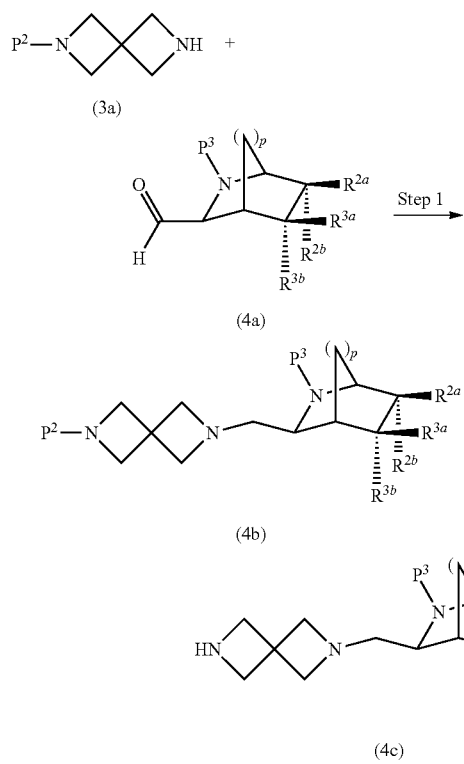

wherein p, $R^{2a}$, $R^{2b}$, $R^{3a}$, and $R^{3b}$ are as defined in Item 1, and P² and P³ are as defined in Preparation Process 3.

Compound (4a) can be prepared by a method described in JP 2007-510619 A, Comprehensive Organic Transformation 2$^{nd}$ Edition (edited by Larock R. C., issued by John Wiley & Sons, Inc., in 1989), etc. or a similar method thereto.

(Step 1)

Compound (4b) can be prepared from compound (3a) and compound (4a) by a method described in J. Am. Chem. Soc., 93(12): 2897-2904 (1971), J. Org. Chem., 37(10): 1673-1674 (1972), J. Org. Chem., 61(11): 3849-3862 (1996), Tetrahedron, 60: 7899-7906 (2004), etc. or a similar method thereto.

(Step 2)

Compound (4c) can be prepared by removing protecting group P² from compound (4b). The present step can be carried out, for example, according to a method described in Protective Groups in Organic Synthesis (edited by Theodora W. Greene, Peter G. M. Wuts, issued by John Wiley & Sons, Inc., in 1999), and the like.

Preparation Process 5

The compound of formula (5d) can be prepared, for example, by the following process:

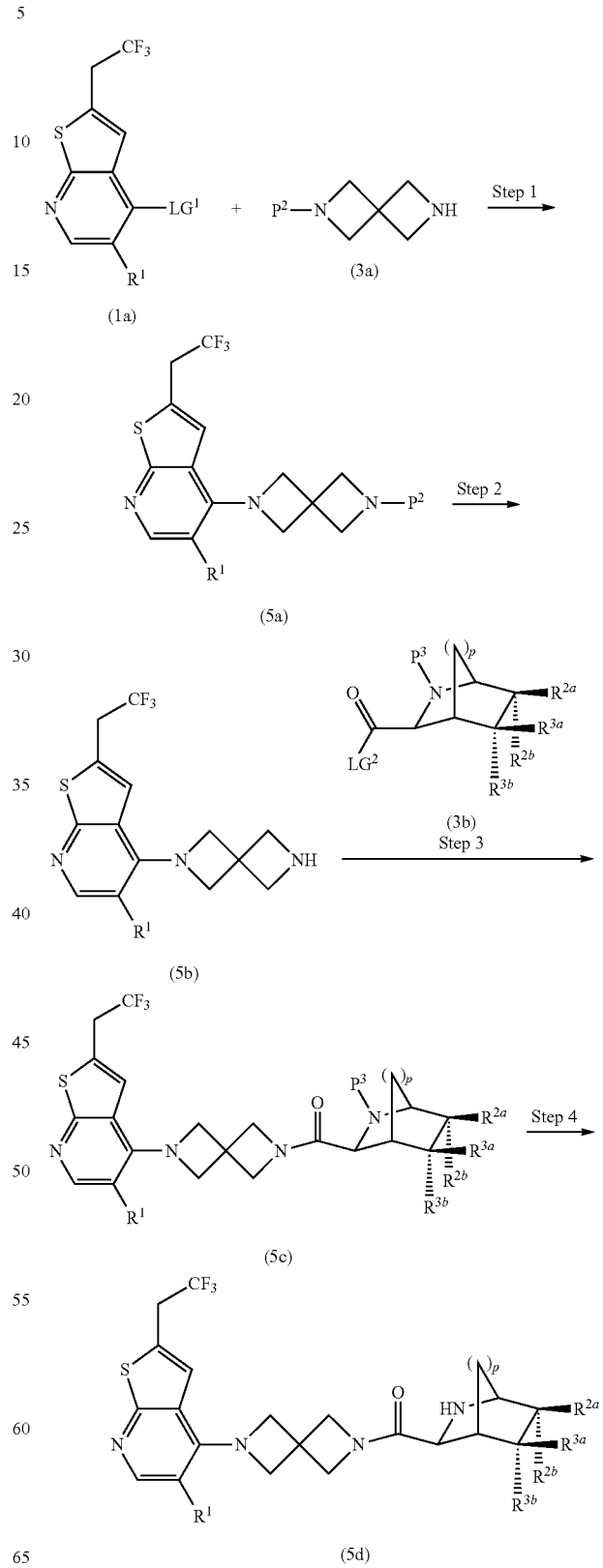

wherein p, $R^1$, $R^{2a}$, $R^{2b}$, $R^{3a}$, and $R^{3b}$ are as defined in Item 1, $LG^1$ is as defined in Preparation Process 2, $LG^2$, is as defined in Preparation Process 3, and $P^2$ and $P^3$ are as defined in Preparation Process 3.

(Step 1)

Compound (5a) can be prepared from compound (1a) and compound (3a) by the method described in step of Preparation Process 1 or a similar method thereto.

(Step 2)

Compound (5b) can be prepared by removing protecting group $P^2$ from compound (5a). The present step can be carried out, for example, according to a method described in Protective Groups in Organic Synthesis (edited by Theodora W. Greene, Peter G. M. Wuts, issued by John Wiley & Sons, Inc., in 1999), and the like.

(Step 3)

Compound (5c) can be prepared from compound (5b) and compound (3b) by the method described in step 1 of Preparation Process 3 or a similar method thereto.

(Step 4)

Compound (5d) can be prepared by removing protecting group $P^3$ from compound (5c). The present step can be carried out, for example, according to a method described in Protective Groups in Organic Synthesis (edited by Theodora W. Greene, Peter C. M. Wuts, issued by John Wiley & Sons, Inc., in 1999), and the like.

Preparation Process 6

The compound of formula (6b) can be prepared, for example, by the following process:

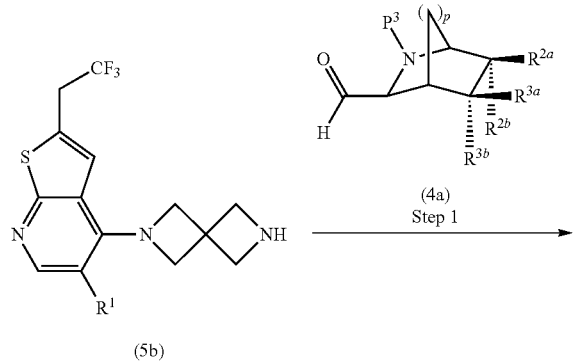

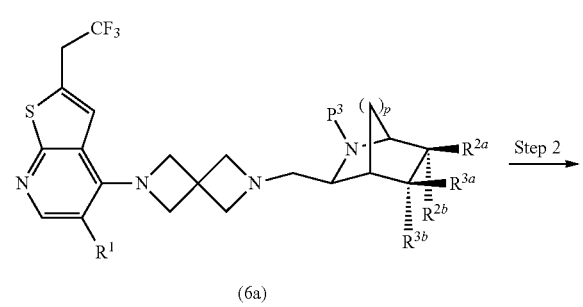

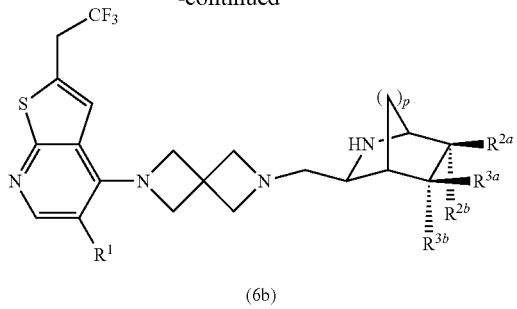

wherein p, $R^1$, $R^{2a}$, $R^{2b}$, $R^{3a}$, and $R^{3b}$ are as defined in Item 1, and $P^3$ is as defined in Preparation Process 4.

(Step 1)

Compound (6a) can be prepared from compound (5b) and compound (4a) by the method described in step 1 of Preparation Process 4 or a similar method thereto.

(Step 2)

Compound (6b) can be prepared by removing protecting group $P^3$ from compound (6a). The present step can be carried out, for example, according to a method described in Protective Groups in Organic Synthesis (edited by Theodora W. Greene, Peter G. M. Wuts, issued by John Wiley & Sons, Inc., in 1999), and the like.

In the above preparation processes, starting materials or intermediates which are not described for preparation processes can be obtained as marketed products, or can be prepared from marketed products by a method well-known to those skilled in the art.

In each reaction described above, protecting groups can be used as necessary, even if the use of protecting groups is not explicitly stated. For example, when any one or more functional groups other than reaction sites are converted to undesired forms under the reaction condition, or the process described above cannot be carried out properly without protecting groups, protecting groups can be used to protect groups other than reaction sites as necessary, and can be deprotected after the reaction is completed or a series of reactions have been carried out to obtain the desired compound.

As such protecting groups, for example, the groups described in T. W. Greene, and P. G. M. Wuts, "*Protective Groups in Organic Synthesis*", John Wiley & Sons, Inc., (1999), and the like may be used. Examples of amino-protecting groups include, for example, benzyloxycarbonyl, tort-butoxycarbonyl, acetyl, benzyl, and the like. Examples of hydroxy-protecting groups include, for example, trialkyl-silyl such as trimethylsilyl and tert-butyldimethylsilyl, acetyl, benzyl, and the like.

The introduction and elimination of protecting groups can be carried out by a method commonly-used in synthetic organic chemistry (for example, see "Protective Groups in Organic Synthesis" described above), or a similar method.

In the present specification, protecting groups, condensing agents and the like may be described in an abbreviated form according to IUPAC-IUB (Biochemical nomenclature committee) commonly-used herein. It should be understood that the names of compounds used in the present specification do not necessarily follow the IUPAC nomenclature.

The intermediates or the desired compounds which are described in the above preparation processes can be transformed to other compounds which fall within the present invention by optionally converting their functional groups to other groups (for example, the conversion from amino, hydroxy, carbonyl, halogen atom, and the like, while protecting or deprotecting other functional groups as necessary). The conversion of functional groups can be carried out by a general method which are commonly used (see, for example, R. C. Larock, "*Comprehensive Organic Transformations*", John Wiley & Sons Inc. (1999)).

The intermediates and the desired compounds described above can be isolated and purified by a purification method commonly-used in organic synthetic chemistry (for example, neutralization, filtration, extraction, washing, drying, enrichment, recrystallization, various chromatography, and the like). In addition, intermediates may be used in next reaction without further purification.

The "pharmaceutically acceptable salt" includes acid addition salts and base addition salts. For example, the acid addition salt includes inorganic acid salts such as hydrochloride, hydrobromide, sulfate, hydroiodide, nitrate, and phosphate; or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. The base addition salt includes inorganic base salts such as sodium salts, potassium salts, calcium salts, magnesium salts, barium salts, and aluminum salts; and organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine, and N,N-dibenzylethylamine. The "pharmaceutically acceptable salt" also includes amino acid salts of basic or acidic amino acids such as arginine, lysine, ornithine, aspartate, and glutamate.

The suitable salts of starting materials and intermediates and the acceptable salts of drug substances are conventional salts. The suitable salt includes, for example, acid addition salts such as organic acid salts (including acetate, trifluoroacetate, maleate, fumarate, citrate, tartrate, methanesulfonate, benzenesulfonate, formate, and toluenesulfonate) and inorganic acid salts (including hydrochloride, hydrobromide, hydroiodide, sulfate, nitrate, and phosphate); salts with amino acids (including arginine, aspartate, and glutamate); alkali metal salts (including sodium salts, and potassium salts); alkaline earth metal salts (including calcium salts, and magnesium salts); ammonium salts; organic base salts (including trimethylamine salts, triethylamine salts, pyridine salts, picolinate, dicyclohexylamine salts, and N,N'-dibenzylethylenediamine salts); and other salts which a person skilled in the art can optionally select.

In the present invention, the compound of formula (1) encompasses deuterated compounds in which any one or more $^1$H in the compound of formula (1) are replaced with $^2$H (D).

The present invention encompasses compounds of formula (1) or pharmaceutically acceptable salts thereof. The compound of the present invention may exist in a form of hydrate and/or solvate of various solvents, including ethanolate, and these hydrate and/or solvate are included in the compound of the present invention.

The compound of the present invention encompasses optical isomers based on an optically active center, atropisomers based on axial or planar chirality caused by restriction of intramolecular rotation, and all other isomers which can exist as stereoisomers, tautomers, and geometric isomers, and crystalline forms in various states, and mixtures thereof.

Especially, each optical isomer and atropisomer can be obtained as a racemate, or as an optically active substance when an optically active starting material or intermediate is used. Racemates of corresponding starting materials, intermediates, or final products can also be physically or chemically resolved into optical enantiomers by a known isolating method such as a method with an optically active column and a fractional crystallization method, at an appropriate step in the above preparation processes, if necessary. These methods for resolving enantiomers include a diastereomer method in which, for example, a racemate is reacted with an optically active resolving agent to synthesize 2 kinds of diastereomers, which are resolved by fractional crystallization or a similar method through different physical properties.

If the compound of the present invention should be obtained as a pharmaceutically acceptable salt thereof, when the compound of formula (1) is obtained as a pharmaceutically acceptable salt, it may be purified without further reaction, and when it is obtained in a free form, it may be dissolved or suspended in an appropriate organic solvent and an acid or base may be added therein to form a salt by a common method.

The different agent which can be used in combination with the compound of the present invention or can be combined with the compound of the present invention includes, for example, at least one anticancer agent selected from the group consisting of an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other anticancer medicaments. Examples of the "different agent which can be used in combination with the compound of the present invention or can be combined with the compound of the present invention" include, for example, azacytidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans-retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, gemtuzumab ozogamicin, inotuzumab ozogamicin, and the like. The above different agent which can be used in combination with the compound of the present invention may also include a cell medicine. The cell medicine which can be used in combination with the compound of the present invention includes, for example, CAR-T cell. It specifically includes tisagenlecleucel, and axicabtagene ciloleucel.

The administration route of the compound of the present invention may be oral, parenteral, intrarectal, or ophthalmic administration, and the daily dose depends on the type of compounds, administration methods, the condition or age of patients, and the like. For example, in the case of oral administration, about 0.01 to 1000 mg, more preferably about 0.1 to 500 mg per kg body weight of a human or mammal can be usually administrated in one to several portions. In the case of parenteral administration such as intravenous injection, for example, about 0.01 mg to 300 mg, more preferably about 1 mg to 100 mg per kg body weight of a human or mammal can be usually administrated.

The compound of the present invention can be orally or parenterally administered directly or as a suitable drug formulation. The dosage form includes, for example, a tablet, a capsule, a powder, a granule, a liquid, a suspension, an injection, a patch, a poultice, and the like, but it is not limited to them. The drug formulation is prepared by a common method using pharmaceutically acceptable additives.

As the additive, an excipient, a disintegrant, a binder, a fluidizer, a lubricant, a coating agent, a solubilizer, a solubilizing adjuvant, a thickener, a dispersant, a stabilizing agent, a sweetening agent, a flavor, and the like may be used, depending on purpose. The additive used herein includes, for example, lactose, mannitol, crystalline cellulose, low-substituted hydroxypropylcellulose, corn starch, partially-pregelatinized starch, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, talc, and the like.

In the present specification, a bond across a ring group as showed in the following formula (W) means that the bond is attached to a substitutable position of the "group". For example, in the case of the following formula (W):

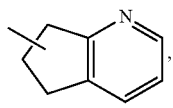
(W)

it represents the following formula (W-1), (W-2), or (W-3):

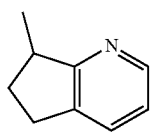
(W-1)

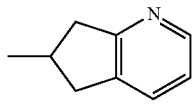
(W-2)

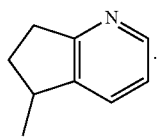
(W-3)

In the present specification, the stereochemistry of substituents in the compound of formula (I) or the example compounds can be illustrated, for example, as follows:

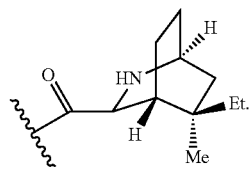 [SMILES: *C(=O)C1N[C@H]2CC[C@@H]1[C@](C)(CC)C2]

In the above structure, the bonds shown as wedged line represent substituents in front of the page; the bond shown as dashed line represents a substituent in back of the page; and when a bond which extends from the ring outside is shown as linear line, it represents that the bond exists either in front or back of the page.

EXAMPLES

The present invention is explained in more detail in the following by referring to Reference examples, Examples, and Tests; however, the technical scope of the present invention should not be limited thereto.

In the present specification, the abbreviations shown below may be used.

THF: tetrahydrofuran

TFA: trifluoroacetic acid

DMF: N,N-dimethylformamide

DMSO: dimethylsulfoxide

MeCN: acetonitrile

WSCI·HCl: 1-(3-dimethylaminopropyl)-3-ethylcarbodiimide hydrochloride

HOBt: 1-hydroxybenzotriazole

Me: methyl

Et: ethyl

Ph: phenyl

Boc: tert-butoxycarbonyl

BINAP: 2,2'-bis(diphenylphosphino)-1,1'-binaphthyl $Pd_2(dba)_3$: tris(dibenzylideneacetone)dipalladium(0)

Ac: acetyl dppf: 1,1'-bis(diphenylphosphino)ferrocene

Xantphos: 4,5-bis(diphenylphosphino)-9,9-dimethylxanthene

Analytical conditions of LC/MS used for identification of compounds are shown below. Observed mass spectrometry value [MS(m/z)] is shown as $[M+H]^+$ or $[M+2H]^{2+}$, and retention time is shown as Rt (min).

The analytical conditions of LC/MS:

Detection apparatus: ACQUITY™ SQ detector (Waters Corporation)

HPLC: ACQUITY™ UPLC system

Column: Waters ACQUITY™ UPLC BEH C18 (1.7 µm, 2.1 mm×30 mm)

Solvent: A: 0.06% formic acid/$H_2O$, B: 0.06% formic acid/MeCN

Gradient condition: 0.0 to 1.3 min Linear gradient from B 2% to 96%

Flow rate: 0.8 mL/min

UV: 220 nm and 254 nm

Reference Example 1

2=4-(2,6-Diazaspiro[3.3]heptan-2-yl)-2-(2,2,2-trifluoroethyl)-5-(trifluoromethyl) thieno[2, 3-b]pyridine

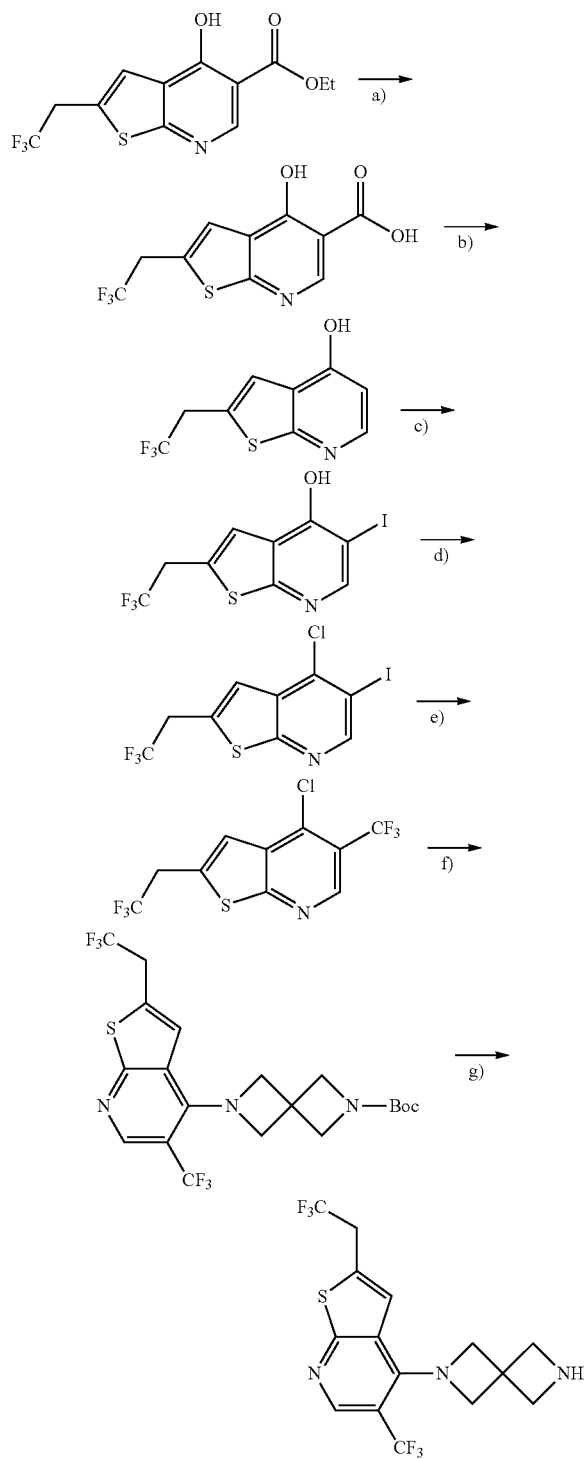

Reference example 1 a) Preparation of 4-hydroxy-2-(2,2,2-trifluoroethyl)thieno[2,3-b]pyridine-5-carboxylic acid Ethyl 4-hydroxy-2-(2,2,2-trifluoroethyl)thieno[2,3-b]pyridine-5-carboxylate (40 g) was suspended in a mixed solvent of THF (200 mL), methanol (100 mL), and water (200 mL). To the mixture was added 4 mol/L aqueous sodium hydroxide (90 mL) at room temperature, and the reaction mixture was stirred at a temperature between room temperature and 40° C. for 5 days. The reaction solution was weakly-acidified with 5 mol/L aqueous hydrochloric acid. The precipitated solid was collected on a filter, and dried at 70° C. in vacuo to give the titled compound (36.9 g).
LC-MS; [M+H]⁻ 278.1/Rt (min) 0.64 b) Preparation of 2-(2,2,2-trifluoroethyl)thieno[2,3-b]pyridin-4-ol

To a solution of 4-hydroxy-2-(2,2,2-trifluoroethyl)thieno[2,3-b]pyridine-5-carboxylic acid (18 g) in quinoline (100 mL) was added copper (0.83 g), and the mixture was stirred at 190° C. for 3 hours. The reaction solution was cooled, and then purified by silica gel column chromatography (eluting with hexane/ethyl acetate, then chloroform/methanol) to give the titled compound (15.2 g).
LC-MS; [M+H]⁺ 234.1/Rt (min) 0.54 c) Preparation of 5-iodo-2-(2,2,2-trifluoroethyl)thieno[2,3-b]pyridin-4-ol

To a suspension of 2-(2,2,2-trifluoroethyl)thieno[2,3-b]pyridin-4-ol (30 g) in acetonitrile (322 mL) was added N-iodosuccinimide (32 g) at room temperature, and the mixture was stirred under reflux for 2 hours. The reaction mixture was cooled to 0° C. The precipitated solid was collected on a filter, and washed with acetonitrile and then hexane to give the titled compound (46.2 g).
LC-MS; [M+H]⁻ 360.0/Rt (min) 0.65 d) Preparation of 4-chloro-5-iodo-2-(2,2,2-trifluoroethyl)thieno[2,3-b]pyridine 5-Iodo-2-(2,2,2-trifluoroethyl)thieno[2,3-b]pyridin-4-ol (46 g) was added to phosphoryl chloride (179 mL) at room temperature, then DMF (0.5 mL) was added thereto, and the mixture was stirred at 70° C. for 2 hours. The reaction solution was allowed to cool to ambient temperature and then concentrated in vacuo. The obtained residue was added to aqueous saturated sodium bicarbonate for quenching. The obtained aqueous solution was extracted with ethyl acetate twice. The obtained organic layer was washed with brine, dried over anhydrous sodium sulfate, and filtrated. The solvent was removed from the filtrate under reduced pressure. The residue was washed with methanol to give the titled compound (33.2 g).
LC-MS; [M+H]⁺ 378.0/Rt (min) 1.19 e) Preparation of 4-chloro-2-(2,2,2-trifluoroethyl)-5-(trifluoromethyl)thieno[2,3-b]pyridine To a solution of 4-chloro-5-iodo-2-(2,2,2-trifluoroethyl)thieno[2,3-b]pyridine (37 g) in DMF (420 mL) was added (1, 10-phenanthroline) (trifluoromethyl) copper (I) (77 g), and the mixture was stirred at 80° C. for 3 hours. The reaction mixture was allowed to cool to ambient temperature, and the insoluble matter was removed by Celite filtration. The Celite was washed with ethyl acetate. To the filtrate were added toluene and ethyl acetate, and the mixture was washed with water (x2), and brine (x1). The obtained organic layer was dried over anhydrous sodium sulfate, and filtrated. The solvent was removed from the filtrate under reduced pressure. The residue was purified by silica gel column chromatography (hexane/ethyl acetate) to give the titled compound (16.9 g).

LC-MS; [M+H]+ 320.0/Rt (min) 1.19 f) Preparation of tert-butyl 6-{2-(2,2,2-trifluoro-ethyl)-5-(trifluoromethyl)thieno[2,3-b]pyridin-4-yl}-2,6-diazaspiro[3.3]heptane-2-carboxylate To a solution of 4-chloro-2-(2,2,2-trifluoroethyl)-5-(trifluoromethyl)thieno[2,3-b]pyridine (16 g) in acetonitrile (100 mL) were added N,N-diisopropylethylamine (52 mL) and tert-butyl 2,6-diazaspiro[3.3]heptane-2-carboxylate 1/2 oxalate (24 g), and the mixture was stirred under reflux for 4 hours. The reaction solution was allowed to cool to ambient temperature, and then a half volume of the solvent was removed under reduced pressure from the reaction solution. Ethyl acetate was added to the concentrated solution, and the mixture was washed with water (x1) and brine (x1). The obtained organic layer was dried over anhydrous sodium sulfate, and filtrated. The solvent was removed from the filtrate under reduced pressure. The residue was purified by silica gel column chromatography (hexane/ethyl acetate) to give the titled compound (21.2 g).

LC-MS; [M+H]⁻ 482.3/Rt (min) 1.16 g) Preparation of 4-(2,6-diazaspiro[3.3]heptan-2-yl)-2-(2,2,2-trifluoroethyl)-5-(trifluoromethyl)thieno[2,3-b]pyridine (Reference example 1)

tert-Butyl 6-{2-(2,2,2-trifluoroethyl)-5-(trifluoromethyl)thieno[2,3-b]pyridin-4-yl}-2,6-diazaspiro[3.3]heptane-2-carboxylate (20 g) was added to TFA (50 mL), and the mixture was stirred at 0° C. for one hour. To the reaction solution was added water, and the mixture was basified with 4 mol/L aqueous sodium hydroxide and extracted with chloroform twice. The obtained organic layer was dried over anhydrous sodium sulfate, and filtrated. The solvent was removed from the filtrate under reduced pressure. The residue was washed with hexane/ethyl acetate to give a crude product of Reference example 1 (9.1 g). In addition, the filtrate was concentrated in vacuo and the residue was purified by silica gel column chromatography (eluting with chloroform/ethyl acetate, then chloroform/methanol) to give the compound of Reference example 1 (5.3 g).

¹H-NMR (400 MHz, DMSO-d6) δ: 8.33 (1H, s), 7.72 (1H, s), 4.64 (4H, br s), 4.04 (2H, d, J=23.6, 9.0 Hz), 3.68 (4H, br s).

LC-MS; [M+H]⁻ 382.2/Rt (min) 0.63

Reference Example 2

4-Chloro-2-(2,2,2-trifluoroethyl)thieno[2,3-b]pyridine-5-carbonitrile

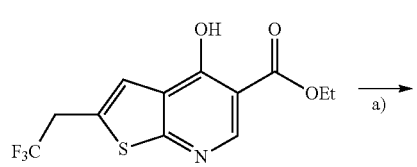

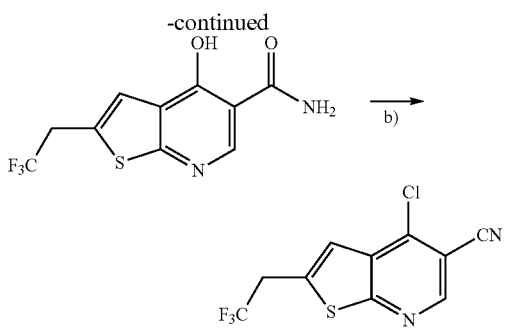

Reference example 2 a) Preparation of 4-hydroxy-2-(2,2,2-trifluoroethyl)thieno[2,3-b]pyridine-5-carboxamide Ethyl 4-hydroxy-2-(2,2,2-trifluoroethyl)thieno[2,3-b]pyridine-5-carboxylate (1.0 g) was added to 8 mol/L ammonia in methanol (10 mL), and the mixture was stirred for 5 hours heating at 100° C. with a microwave device. The obtained reaction solution was concentrated in vacuo to give the titled compound (915 mg). The obtained compound was used without purification in the next reaction.

LC-MS; [M+H]⁻ 277.1/Rt (min) 0.60 b) Preparation of 4-chloro-2-(2,2,2-trifluoroethyl)thieno[2,3-b]pyridine-5-carbonitrile Reference Example 2

To a solution of 4-hydroxy-2-(2,2,2-trifluoroethyl)thieno[2,3-b]pyridine-5-carboxamide (915 mg) obtained as a crude product in chloroform (10 mL) was added phosphoryl chloride (15.4 mL) at 0° C., and the mixture was stirred at 100° C. for 2 hours. The reaction solution was concentrated in vacuo, and the residue was purified by silica gel column chromatography (hexane/ethyl acetate) to give the compound of Reference example 2 (1.02 g).

LC-MS; [M+H]⁺277.0/Rt (min) 0.97

Reference Example 3

4-(2,6-Diazaspiro[3.3]heptan-2-yl)-2-(2,2,2-trifluoroethyl) thieno[2, 3-b]pyridine-5-carbonitrile

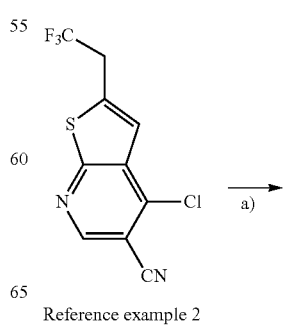

Reference example 2

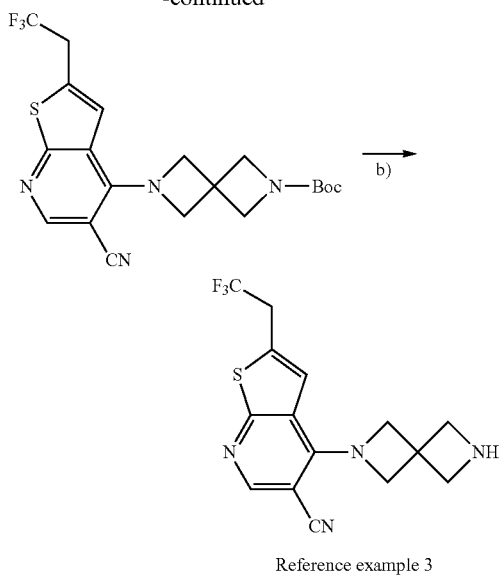

Reference example 3 a) Preparation of tert-butyl 6-[5-cyano-2-(2,2,2-trifluoroethyl)thieno[2,3-b]pyridin-4-yl]-2,6-diazaspiro[3.3]heptane-2-carboxylate To a solution of 4-chloro-2-(2,2,2-trifluoroethyl)thieno[2,3-b]pyridine-5-carbonitrile (1.02 g) in acetonitrile (20 mL) were added tert-butyl 2,6-diazaspiro[3.3]heptane-2-carboxylate hemioxalate (1.79 g) and N,N-diisopropylethylamine (3.22 mL), and the mixture was stirred under reflux for 3 hours. To the reaction solution was added aqueous saturated ammonium chloride, and the mixture was extracted with ethyl acetate. The organic layer was dried over sodium sulfate, and filtrated. The solvent was removed from the filtrate under reduced pressure. The residue was purified by silica gel column chromatography (hexane/ethyl acetate) to give the titled compound (1.18 g).

LC-MS; [M+H]$^+$439.3/Rt (min) 1.03 b) Preparation of 4-(2,6-diazaspiro[3.3]heptan-2-yl)-2-(2,2,2-trifluoroethyl)thieno[2,3-b]pyridine-5-carbonitrile Reference Example 3

To a solution of tert-butyl 6-[5-cyano-2-(2,2,2-trifluoroethyl)thieno[2,3-b]pyridin-4-yl]-2,6-diazaspiro[3.3]heptane-2-carboxylate (1.18 g) in chloroform (18 mL) was added trifluoroacetic acid (3.11 mL) at 0° C., and the mixture was stirred at room temperature for 3 hours. The reaction solution was concentrated in vacuo, and the residue was purified by amino silica gel column chromatography (chloroform/methanol) to give the compound of Reference example 3 (866 mg).

$^1$H-NMR (400 MHz, DMSO-d6) δ: 8.27 (1H, s), 7.59 (1H, s), 4.71 (4H, br s), 4.05 (2H, d, J=22.8, 11.6 Hz), 3.63 (4H, br s).

LC-MS; [M+H]$^+$339.2/Rt (min) 0.65

Reference Example 4

4-(2,6-Diazaspiro[3.3]heptan-2-yl)-5-(difluoromethyl)-2-(2,2,2-trifluoroethyl) thieno[2,3-b]pyridine

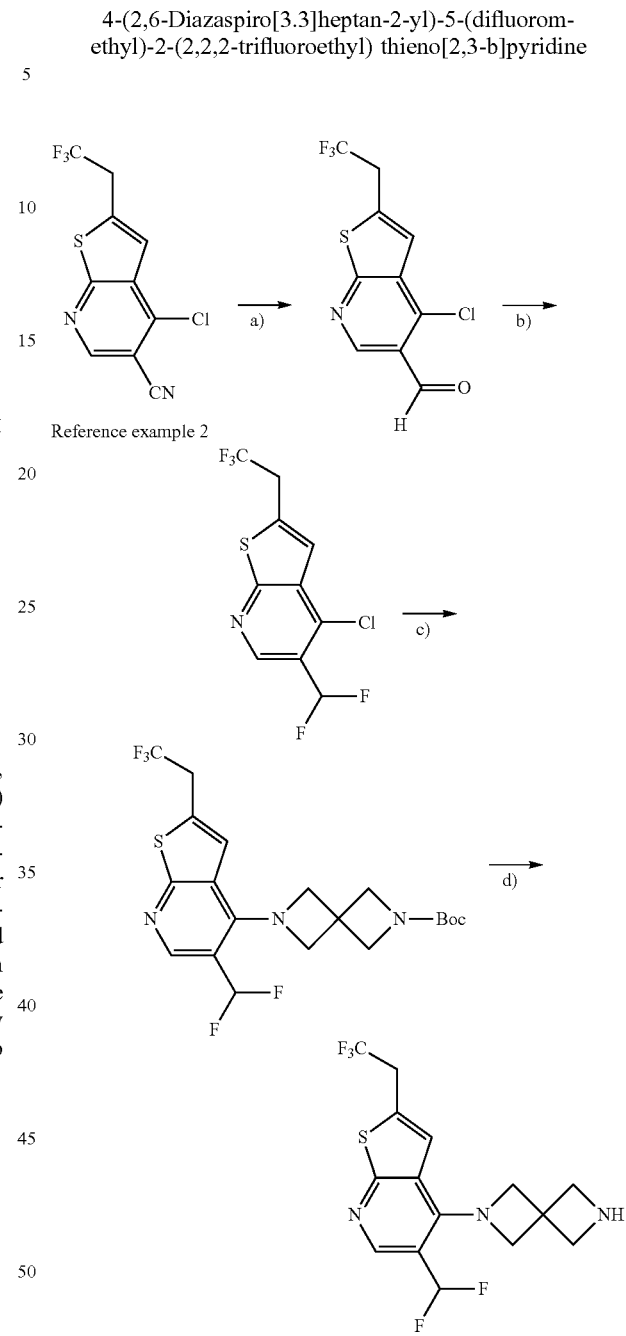

Reference example 4 a) Preparation of 4-chloro-2-(2,2,2-trifluoroethyl)thieno[2,3-b]pyridine-5-carboaldehyde To a solution of 4-chloro-2-(2,2,2-trifluoroethyl)thieno[2,3-b]pyridine-5-carbonitrile (1.50 g) in dichloromethane (20 mL) was added 1 mol/L diisobutylaluminium hydride (6.0 mL) at −78° C., and the mixture was stirred at 0° C. for 2 hours. To the reaction solution was added aqueous saturated ammonium chloride, and the mixture was extracted with ethyl acetate. The organic layer was dried over sodium sulfate, and filtrated. The solvent was removed from the filtrate under reduced pressure. The residue was purified by silica gel column chromatography (hexane/ethyl acetate) to give the titled compound (1.0 g).
LC-MS; [M+H]⁻ 280.0/Rt (min) 0.97 b) Preparation of 4-chloro-5-(difluoromethyl)-2-(2,2,2-trifluoroethyl)thieno[2,3-b]pyridine To a solution of 4-chloro-2-(2,2,2-trifluoroethyl)thieno[2,3-b]pyridine-5-carboaldehyde (910 mg) in dichloromethane (10 mL) was added N,N-diethylaminosulfur trifluoride (0.43 mL) dropwise at 0° C., and the mixture was stirred at a temperature between 0° C. and room temperature overnight. The reaction solution was added dropwise to aqueous saturated sodium bicarbonate at 0° C., and the obtained solution was extracted with chloroform twice. The obtained organic layer was dried over anhydrous sodium sulfate, and filtrated. The solvent was removed from the filtrate under reduced pressure. The residue was purified by silica gel column chromatography (hexane/ethyl acetate) to give the titled compound (730 mg).
LC-MS; [M+H]⁺ 302.2/Rt (min) 1.12 c) Preparation of tert-butyl 6-{5-(difluoromethyl)-2-(2,2,2-trifluoroethyl)thieno[2,3-b]pyridin-4-yl}-2,6-diazaspiro[3.3]heptane-2-carboxylate To a solution of 4-chloro-5-(difluoromethyl)-2-(2,2,2-trifluoroethyl)thieno[2,3-b]pyridine (730 mg) in acetonitrile (10 mL) were added N,N-diisopropylethylamine (4.2 mL) and tert-butyl 2,6-diazaspiro[3.3]heptane-2-carboxylate 1/2 oxalate (1.78 g), and the mixture was stirred under reflux for 2 days. The reaction solution was allowed to cool to ambient temperature, and then a half volume of the solvent was removed under reduced pressure from the reaction solution. Ethyl acetate was added to the concentrated solution, and the mixture was washed with water (x1) and brine (x1). The obtained organic layer was dried over anhydrous sodium sulfate, and filtrated. The solvent was removed from the filtrate under reduced pressure. The residue was purified by silica gel column chromatography (hexane/ethyl acetate) to give the titled compound (610 mg).
LC-MS; [M+H]⁻ 464.3/Rt (min) 1.03 d) Preparation of 4-(2,6-diazaspiro[3.3]heptan-2-yl)-5-(difluoromethyl)-2-(2,2,2-trifluoroethyl)thieno[2,3-b]pyridine (Reference example 4)

To a solution of tert-butyl 6-{5-(difluoromethyl)-2-(2,2,2-trifluoroethyl)thieno[2,3-b]pyridin-4-yl}-2,6-diazaspiro[3.3]heptane-2-carboxylate (610 mg) in dichloromethane (9.0 mL) was added TFA (1.0 mL), and the mixture was stirred at 0° C. for one hour. To the reaction solution was added water, and the mixture was basified with 4 mol/L aqueous sodium hydroxide and extracted with chloroform twice. The obtained organic layer was dried over anhydrous sodium sulfate, and filtrated. The solvent was removed from the filtrate under reduced pressure. The residue was purified by amine silica gel column chromatography (chloroform/methanol) to give the compound of Reference example 4 (350 mg).
LC-MS; [M+H]⁻ 364.2/Rt (min) 0.66

Reference Example 5

(1S,3S,4S,5R)-2-(tert-Butoxycarbonyl)-5-hydroxy-2-azabicyclo[2.2.2]octane-3-carboxylic acid Reference Example 6

(1S,3S,4R,6S)-2-(tert-Butoxycarbonyl)-6-hydroxy-2-azabicyclo[2.2.2]octane-3-carboxylic acid

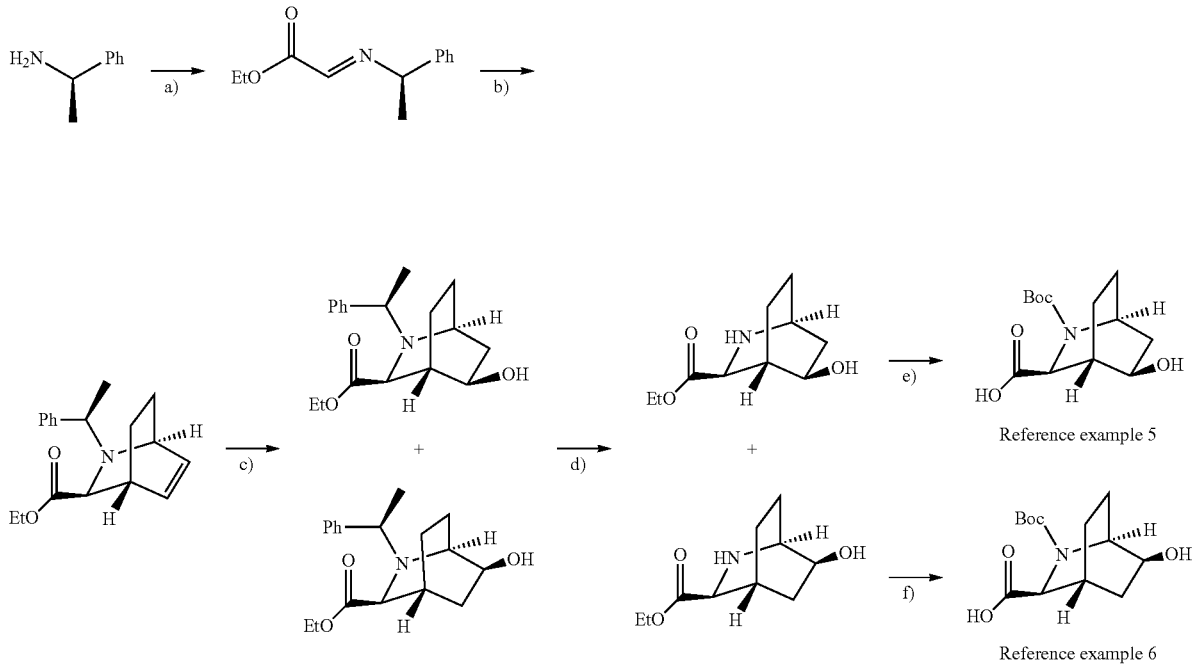

a) Preparation of ethyl (2E)-{[(1R)-1-phenylethyl]imino}acetate

To (R)-1-phenylethylamine (63 mL) was added ethyl oxoacetate (100 mL), and the mixture was stirred at room temperature for one hour. The mixture was concentrated in vacuo to give the titled compound. The obtained product was used without purification in the next reaction.

b) Preparation of ethyl (1S,3S,4R)-2-[(1R)-1-phenylethyl]-2-azabicyclo[2.2.2]oct-5-ene-3-carboxylate To a solution of ethyl (2E)-{[(1R)-1-phenylethyl]imino}acetate prepared in the above step in dichloromethane (475 mL) was added molecular sieves 4A (powder, 10 g), and the reaction solution was cooled to −70°. To the cooled reaction solution were added trifluoroacetic acid (32 mL) and boron trifluoride diethyl ether complex (53 mL) dropwise, and the mixture was stirred for 15 minutes. To the reaction solution was added 1,3-cyclohexadiene (42 mL) dropwise, and the reaction solution was warmed to room temperature, and stirred overnight. To the reaction solution was added aqueous saturated sodium bicarbonate, and the mixture was extracted with ethyl acetate. The organic layer was washed with aqueous saturated sodium bicarbonate, dried over sodium sulfate, and filtrated. The solvent was removed from the filtrate under reduced pressure. The residue was purified by silica gel column chromatography (hexane/ethyl acetate) to give the titled compound (59.4 g).
LC-MS; [M+H]⁻ 286.2/Rt (min) 0.533 c) Preparation of a mixture of ethyl (1S,3S,4S,5R)-5-hydroxy-2-[(1R)-1-phenylethyl]-2-azabicyclo[2.2.2]octane-3-carboxylate and ethyl (1S,3S,4R,6S)-6-hydroxy-2-[(1R)-1-phenylethyl]-2-azabicyclo[2.2.2]octane-3-carboxylate To a solution of ethyl (1S,3S,4R)-2-[(1R)-1-phenylethyl]-2-azabicyclo[2.2.2]oct-5-ene-3-carboxylate (85.5 g) in THF (500 mL) was added 1.0 mol/L borane-THF complex (300 mL) dropwise at 0 to 5° C., and the mixture was stirred at room temperature overnight. To the reaction solution were added 3 mol/L aqueous sodium hydroxide (62 mL) and 30% hydrogen peroxide water (62 mL) under ice temperature, and the reaction solution was stirred for 30 minutes. And, aqueous sodium thiosulfate was added thereto, and the mixture was stirred for one hour. The reaction solution was extracted with ethyl acetate/chloroform, and the organic layer was washed with brine. The organic layer was dried over sodium sulfate, and filtrated. The solvent was removed from the filtrate under reduced pressure. The residue was purified by silica gel column chromatography (hexane/ethyl acetate) to give the titled compound (51.7 g).
LC-MS; [M+H]⁺304.2/Rt (min) 0.532 d) Preparation of ethyl (1S,3S,4S,5R)-5-hydroxy-2-azabicyclo[2.2.2]octane-3-carboxylate and ethyl (1S,3S,4R,6S)-6-hydroxy-2-azabicyclo[2.2.2]octane-3-carboxylate To a solution of the above product (51.7 g) in ethanol (500 mL) was added 10% palladium hydroxide (10.2 g), and the mixture was stirred under pressurized hydrogen atmosphere (0.3-0.4 MPa) at room temperature for 6 hours. The reaction mixture was filtrated, and the filtrate was concentrated in vacuo. The residue was purified by silica gel column chromatography (chloroform/methanol) to give ethyl (1S,3S,4S,5R)-5-hydroxy-2-azabicyclo[2.2.2]octane-3-carboxylate (19.0 g) and ethyl (1S,3S,4R,6S)-6-hydroxy-2-azabicyclo[2.2.2]octane-3-carboxylate (5.05 g) which are the titled compounds.
ethyl (1S,3S,4S,5R)-5-hydroxy-2-azabicyclo[2.2.2]octane-3-carboxylate
LC-MS; [M+H]⁻ 200.2/Rt (min) 0.265
ethyl (1S,3S,4R,6S)-6-hydroxy-2-azabicyclo[2.2.2]octane-3-carboxylate
LC-MS; [M+H]⁻ 200.1/Rt (min) 0.361 e) Preparation of (1S,3S,4S,5R)-2-(tert-butoxycarbonyl)-5-hydroxy-2-azabicyclo[2.2.2]octane-3-carboxylic acid

Reference Example 5

To a solution of ethyl (1S,3S,4S,5R)-5-hydroxy-2-azabicyclo[2.2.2]octane-3-carboxylate (10.48 g) in 1,4-dioxane (153 mL) was added 1 mol/L aqueous sodium hydroxide (238 mL), and the mixture was stirred at room temperature for one hour. Then, the reaction solution was cooled to 0° C., and di-tert-butyl dicarbonate (11.48 g) was added thereto. The reaction solution was stirred for one hour, and then acidified with 1 mol/L aqueous hydrochloric acid. To the acidified solution was added brine, and the mixture was extracted with 10% ethanol/chloroform mixture. The organic layer was dried over sodium sulfate, and filtrated. The solvent was removed from the filtrate under reduced pressure. The residue was washed with diisopropyl ether. The precipitate was collected on a filter and dried to give the compound of Reference example 5 (8.40 g).
¹H-NMR (DMSO-D₆) δ: 12.55 (1H, br s), 4.86 (1H, br s), 3.96-3.81 (3H, m), 2.09-1.69 (4H, m), 1.59-1.49 (1H, m), 1.36 (3H, s), 1.31 (6H, s), 1.29-1.17 (2H, m).

f) Preparation of (1S,3S,4R,6S)-2-(tert-butoxycarbonyl)-6-hydroxy-2-azabicyclo[2.2.2]octane-3-carboxylic acid

Reference Example 6

The compound of Reference example 6 (1.60 g) was prepared according to a similar procedure to step e) by using ethyl (1S,3S,4R,6S)-6-hydroxy-2-azabicyclo[2.2.2]octane-3-carboxylate.
¹H-NMR (DMSO-D₆) δ: 4.09-4.05 (3H, m), 2.28-2.20 (1H, m), 2.18-2.05 (2H, m), 1.91-1.80 (1H, m), 1.63-1.50 (3H, m), 1.45 (3H, s), 1.40 (6H, s).

Reference Example 7

(1S,3S,4S,5R)-2-(tert-Butoxycarbonyl)-5-hydroxy-2-azabicyclo[2.2.1]heptane-3-carboxylic acid

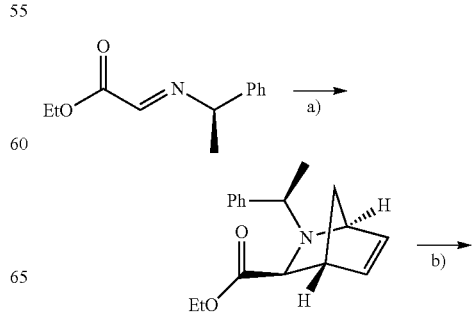

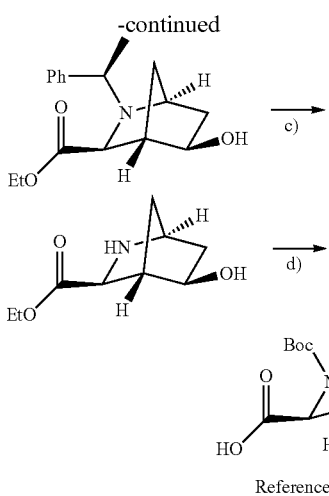

a) Preparation of ethyl (1S,3S,4R)-2-[(1R)-1-phenylethyl]-2-azabicyclo[2.2.1]hept-5-ene-3-carboxylate The titled compound (10.8 g) was prepared according to a similar procedure to step b) of Reference example 5, Reference example 6 by using ethyl (2E)-{[(1R)-1-phenylethyl]imino}acetate (12.0 g) and cyclopentadiene (4.92 mL).
LC-MS; [M+H]⁺ 272.2/Rt (min) 0.540 b) Preparation of ethyl (1S,3S,4S,5R)-5-hydroxy-2-[(1R)-1-phenylethyl]-2-azabicyclo[2.2.1]heptane-3-carboxylate (10.8 g)

The titled compound (7.49 g) was prepared according to a similar procedure to step c) of Reference example 5, Reference example 6 by using ethyl (1S,3S,4R)-2-[(1R)-1-phenylethyl]-2-azabicyclo[2.2.1]hept-5-ene-3-carboxylate (10.8 g).
LC-MS; [M+H]⁻ 290.2/Rt (min) 0.461 c) Preparation of ethyl (1S,3S,4S,5R)-5-hydroxy-2-azabicyclo[2.2.1]heptane-3-carboxylate The titled compound (2.89 g) was prepared according to a similar procedure to step d) of Reference example 5, Reference example 6 by using ethyl (1S,3S,4S,5R)-5-hydroxy-2-[(1R)-1-phenylethyl]-2-azabicyclo[2.2.1]heptane-3-carboxylate (7.49 g).
LC-MS; [M+H]⁻ 186.1/Rt (min) 0.267 d) Preparation of (1S,3S,4S,5R)-2-(tert-butoxycarbonyl)-5-hydroxy-2-azabicyclo[2.2.1]heptane-3-carboxylic acid Reference Example 7

The compound of Reference example 7 (980 mg) was prepared according to a similar procedure to step e) of Reference example 5, Reference example 6 by using ethyl (1S,3S,4S,5R)-5-hydroxy-2-azabicyclo[2.2.1]heptane-3-carboxylate (2.88 g). ¹H-NMR (DMSO-D₆) δ: 4.99 (1H, br s), 4.11-3.95 (1H, m), 3.95-3.82 (1H, m), 3.48-3.40 (1H, m), 2.41-2.31 (1H, m), 1.90-1.75 (1H, m), 1.69-1.49 (2H, m), 1.45-1.19 (10H, m).

Reference Example 8 tert-Butyl (1S,3S,4S,5R)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate Reference Example 9 tert-Butyl (1S,3S,4S,5S)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate

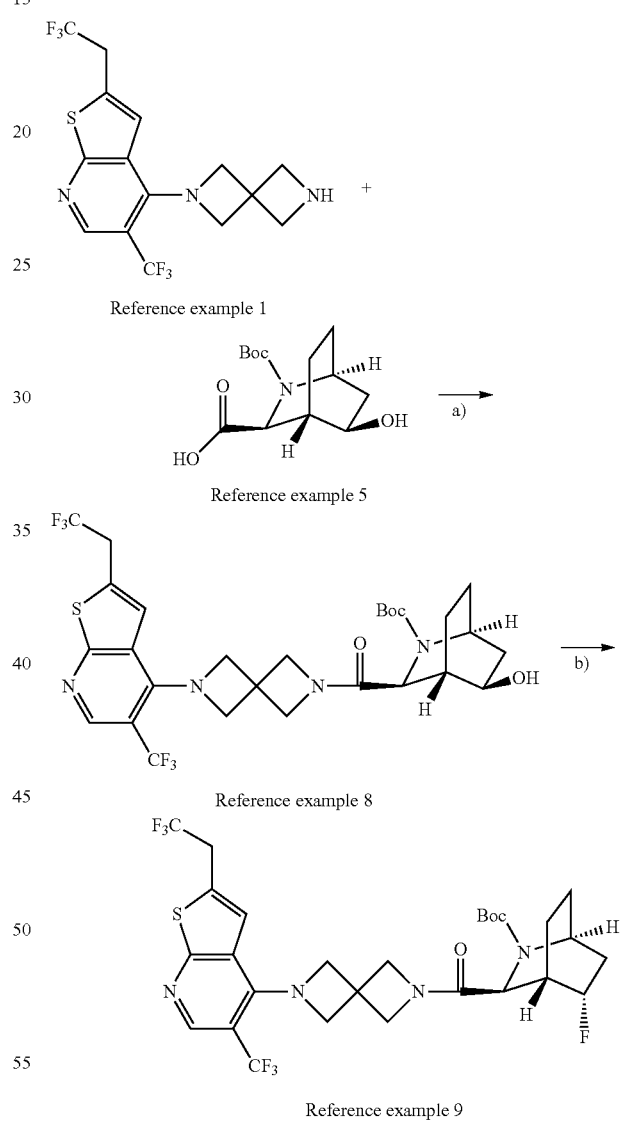

a) Preparation of tert-butyl (1S,3S,4S,5R)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 8)

To a solution of 4-(2,6-diazaspiro[3.3]heptan-2-yl)-2-(2,2,2-trifluoroethyl)-5-(trifluoromethyl)thieno[2,3-b]pyridine (1.52 g) prepared in Reference example 1 in DMF (10 mL) were added (1S,3S,4S,5R)-2-(tert-butoxycarbonyl)-5-hydroxy-2-azabicyclo[2.2.2]octane-3-carboxylic acid (1.30 g) prepared in Reference example 5, WSCI·HCl (0.92 g), HOBt (0.65 g), and triethylamine (0.67 mL), and the mixture was stirred at room temperature for 2 hours. To the reaction solution was added ethyl acetate, and the mixture was washed with water (x2), and brine (x1). The obtained organic layer was dried over anhydrous sodium sulfate, and filtrated. The solvent was removed from the filtrate under reduced pressure. The residue was washed with chloroform/diethyl ether/hexane (1/1/1) to give the compound of Reference example 8 (2.51 g).

LC-MS; [M+H]⁻ 635.4/Rt (min) 0.95 b) Preparation of tert-butyl (1S,3S,4S,5S)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 9)

To a solution of tert-butyl (1S,3S,4S,5R)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (6 g) in dichloromethane (63 mL) was added N,N-diethylaminosulfur trifluoride (2.5 mL) dropwise at 0° C., and the mixture was stirred at a temperature between 0° C. and room temperature overnight. To the reaction solution was added aqueous saturated sodium bicarbonate dropwise at 0° C., and the obtained solution was extracted with chloroform twice. The obtained organic layer was dried over anhydrous sodium sulfate, and filtrated. The solvent was removed from the filtrate under reduced pressure. The residue was purified by silica gel column chromatography (chloroform/ethyl acetate) to give the compound of Reference example 9 (1.45 g). ¹H-NMR (400 MHz, DMSO-d6) δ: 8.35 and 8.31 (total 1H, each s), 7.71 (1H, s), 4.96 (1H, m), 4.79-4.69 (4H, m), 4.44 (0.5H, m), 4.36 (1.5H, br s), 4.22 (1H, br s), 4.18-3.99 (5H, m), 2.38 (0.3H, br s), 2.31 (0.7H, m), 2.05 (1H, m), 1.83 (1H, m), 1.76-1.50 (2H, m), 1.38 (3.5H, br s), 1.35 (6.5H, br s), 1.23 (1H, m), LC-MS; [M+H]⁺637.4/Rt (min) 1.12

Reference Example 10 tert-Butyl (1S,3S,4S,5S)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.1]heptane-2-carboxylate

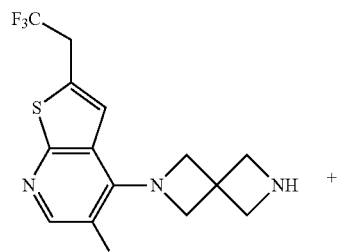

Reference example 1

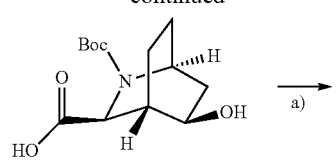

Reference example 7

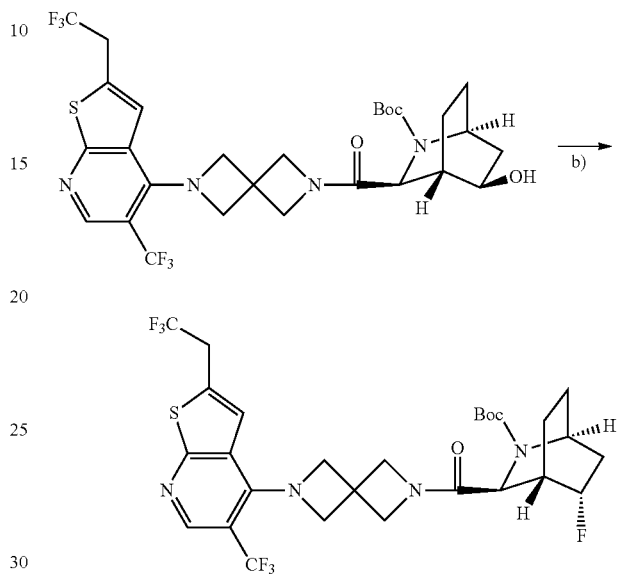

Reference example 10 a) Preparation of tert-butyl (1S,3S,4S,5R)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.1]heptane-2-carboxylate The titled compound (470 mg) was prepared according to a similar procedure to step a) of Reference example 9 by using 4-(2,6-diazaspiro[3.3]heptan-2-yl)-2-(2,2,2-trifluoroethyl)-5-(trifluoromethyl)thieno[2,3-b]pyridine (300 mg) obtained in Reference example 1 and (1S,3S,4S,5R)-2-(tert-butoxycarbonyl)-5-hydroxy-2-azabicyclo[2.2.1]heptane-3-carboxylic acid (202 mg) obtained in Reference example 7.

LC-MS; [M+H]⁻ 621.4/Rt (min) 0.95 b) Preparation of tert-butyl (1S,3S,4S,5S)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.1]heptane-2-carboxylate (Reference example 10)

The compound of Reference example 10 (112 mg) was prepared according to a similar procedure to step b) of Reference example 9 by using tert-butyl (1S,3S,4S,5R)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.1]heptane-2-carboxylate (200 mg).

LC-MS; [M+H]⁺ 623.5/Rt (min) 1.04

Reference Example 11 tert-Butyl (1S,3S,4S)-5-oxo-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate

Reference Example 12 tert-Butyl (1S,3S,4S)-5,5-difluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate

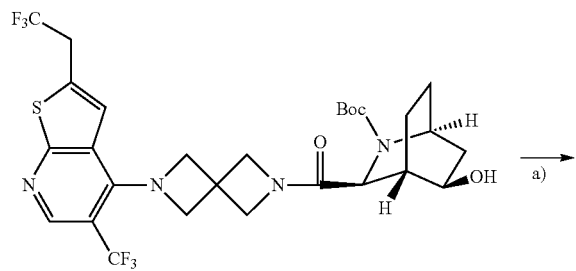

Reference example 8

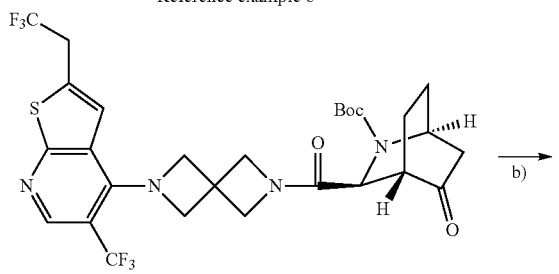

Reference example 11

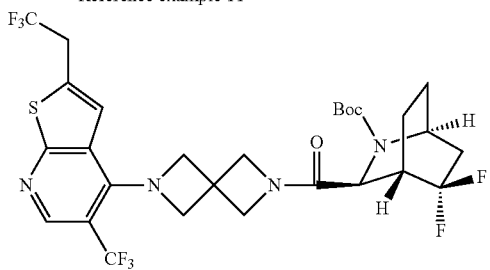

Reference example 12 a) Preparation of tert-butyl (1S,3S,4S)-5-oxo-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 11)

To a solution of tert-butyl (1S,3S,4S,5R)-5-hydroxy-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (0.14 g) prepared in Reference example 8 in dichloromethane (2.1 mL) was added Dess-Martin reagent (0.14 g), and the mixture was stirred at room temperature overnight. The insoluble matter in the reaction solution was removed by Celite filtration. The Celite was washed with chloroform. The obtained organic layer was concentrated in vacuo, and the residue was purified by silica gel column chromatography (chloroform/methanol) to give the compound of Reference example 11 (0.12 g).

LC-MS; [M+H]$^+$ 633.4/Rt (min) 1.02 b) Preparation of tert-butyl (1S,3S,4S)-5,5-difluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 12)

To a solution of Reference example 11 (65 mg) in dichloromethane (1 mL) was added N,N-diethylaminosulfur trifluoride (41 µL) dropwise at 0° C., and the mixture was stirred at a temperature between 0° C. and room temperature overnight. And, N,N-diethylaminosulfur trifluoride (122 µL) was added thereto dropwise at 0° C., and the mixture was stirred at a temperature between 0° C. and room temperature overnight. To the reaction solution was added dropwise aqueous saturated sodium bicarbonate, and the obtained solution was extracted with chloroform twice. The obtained organic layer was dried over anhydrous sodium sulfate, and filtrated. The solvent was removed from the filtrate under reduced pressure. The residue was purified by silica gel column chromatography (chloroform/methanol) to give the compound of Reference example 12 (56 mg).

LC-MS; [M+H]$^-$ 655.4/Rt (min) 1.16

Reference Example 13 tert-Butyl (1S,3S,4R,6S)-6-[(prop-2-en-1-yl)oxy]-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate

Reference Example 14 tert-Butyl (1S,3R,4R,6S)-6-[(prop-2-en-1-yl)oxy]-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate Reference example 13

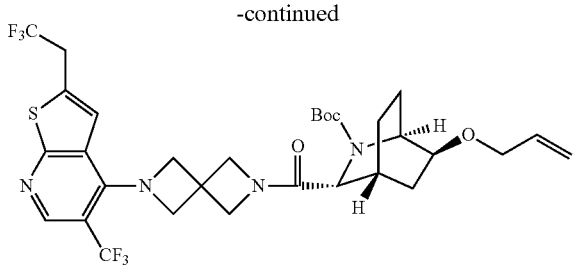

Reference example 14 a) Preparation of 2-tert-butyl 3-ethyl (1S,3S,4R, 6S)-6-[(prop-2-en-1-yl)oxy]-2-azabicyclo[2.2.2]octane-2,3-dicarboxylate To a solution of ethyl (1S,3S,4R,6S)-6-hydroxy-2-azabicyclo[2.2.2]octane-3-carboxylate (400 mg) in THF (10 mL) were added di-tert-butyl dicarbonate (1.00 g) and sodium carbonate (700 mg), and the mixture was stirred at room temperature for one hour. To the reaction solution was added ethyl acetate, and the mixture was washed with water (x2), and brine (x1). The organic layer was dried over anhydrous sodium sulfate, and filtrated. The solvent was removed from the filtrate under reduced pressure. A solution of the residue in THF (10 mL) was cooled to 0° C., and then sodium hydride (88 mg) and allyl bromide (233 μL) were added to the solution. The solution was stirred at room temperature for 24 hours. To the reaction solution were added aqueous saturated ammonium chloride and ethyl acetate, and the mixture was washed with water (x2) and brine (x1). The obtained organic layer was dried over anhydrous sodium sulfate, and filtrated. The solvent was removed from the filtrate under reduced pressure. The residue was purified by silica gel column chromatography (hexane/ethyl acetate) to give the titled compound (120 mg).
LC-MS; [M+H]⁻ 340.4/Rt (min) 1.21 b) Preparation of tert-butyl (1S,3S,4R,6S)-6-[(prop-2-en-1-yl)oxy]-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 13) and tert-butyl (1S,3R,4R,6S)-6-[(prop-2-en-1-yl)oxy]-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (Reference example 14)

To a solution of 2-tert-butyl 3-ethyl(1S,3S,4R,6S)-6-[(prop-2-en-1-yl)oxy]-2-azabicyclo[2.2.2]octane-2,3-dicarboxylate (120 mg) in a mixed solvent of THF (5 mL) and water (1 mL) was added 2 mol/L aqueous sodium hydroxide (1 mL) at 0° C., and the mixture was refluxed for 12 hours. And, the mixture was stirred at a temperature between 0° C. and room temperature overnight. To the reaction solution were added aqueous saturated ammonium chloride and ethyl acetate, and the mixture was washed with water (x2), and brine (x1). The obtained organic layer was dried over anhydrous sodium sulfate, and filtrated. The solvent was removed from the filtrate under reduced pressure. A solution of the residue in dichloromethane (10 mL) was cooled to 0° C., and then 4-(2,6-diazaspiro[3.3]heptan-2-yl)-2-(2,2,2-trifluoroethyl)-5-(trifluoromethyl)thieno[2,3-b]pyridine (129 mg) prepared in Reference example 1, WSCI·HCl (200 mg), HOBt (150 mg), and triethylamine (0.30 mL) were added to the solution. The solution was stirred at room temperature for 2 hours. To the reaction solution was added ethyl acetate, and the mixture was washed with water (x2), and brine (x1). The obtained organic layer was dried over anhydrous sodium sulfate, and filtrated. The solvent was removed from the filtrate under reduced pressure. The residue was purified by silica gel column chromatography (hexane/ethyl acetate) to give the compounds of Reference example 13 (88 mg) and Reference example 14 (43 mg).

Reference Example 13

LC-MS; [M+H]⁺ 675.5/Rt (min) 1.25

Reference Example 14

LC-MS; [M+H]⁺ 675.5/Rt (min) 1.25

Reference Examples 15-35

The following Reference examples 15 to 35 were prepared according to similar methods to Reference examples 8 to 14 by using each corresponding starting compound.

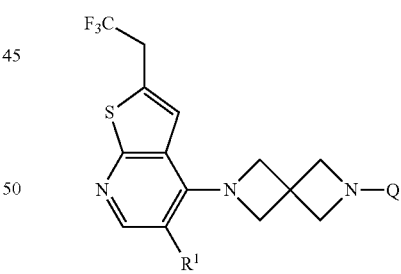

| Reference example | R¹ | Q | LC-MS: [M + H]⁺/ Rt (min) |
|---|---|---|---|
| 15 | CF₃ | Boc-N, H (structure) | 605.5/1.11 |

-continued

| Reference example | R¹ | Q | LC-MS: [M + H]⁺/ Rt (min) |
|---|---|---|---|
| 16 | CF₃ | *(structure)* | 619.5/1.11 |
| 17 | CF₃ | *(structure)* | 649.4/1.00 |
| 18 | CF₃ | *(structure)* | 635.4/0.97 |
| 19 | CF₃ | *(structure)* | 637.5/1.13 |
| 20 | CF₃ | *(structure)* | 725.2/1.26 |
| 21 | CF₃ | *(structure)* | 725.2/1.26 |
| 22 | CF₃ | *(structure)* | 655.4/1.12 |
| 23 | CF₃ | *(structure)* | 633.4/1.02 |
| 24 | CF₃ | *(structure)* | 649.4/0.98, 1.00 |
| 25 | CF₃ | *(structure)* | 725.4/1.26 |

-continued

| Reference example | R[1] | Q | LC-MS: [M + H]+/ Rt (min) |
|---|---|---|---|
| 26 | CF$_3$ | (structure with Boc-N bicyclic, OH) | 635.4/0.96 |
| 27 | CN | (structure with Boc-N bicyclic) | 576.4/1.02/ |
| 28 | CN | (structure with Boc-N bicyclic) | 562.4/0.99 |
| 29 | CN | (structure with Boc-N bicyclic, F) | 594.4/0.99 |
| 30 | CN | (structure with Boc-N bicyclic, F, F) | 612.4/1.04 |
| 31 | CN | (structure with Boc-N bicyclic, OH, Me) | 606.4/0.92 |
| 32 | CN | (structure with Boc-N bicyclic, =O) | 590.4/0.92 |
| 33 | CHF$_2$ | (structure with Boc-N bicyclic) | 601.4/1.00 |
| 34 | CHF$_2$ | (structure with Boc-N bicyclic) | 587.4/0.97 |

-continued

| Reference example | R¹ | Q | LC-MS: [M + H]⁺/ Rt (min) |
|---|---|---|---|
| 35 | CF₃ | 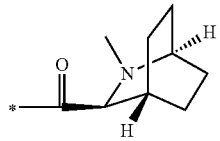 | 267.9/0.79 |

Example 1

{(1S,3S,4S,5S)-5-Fluoro-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone

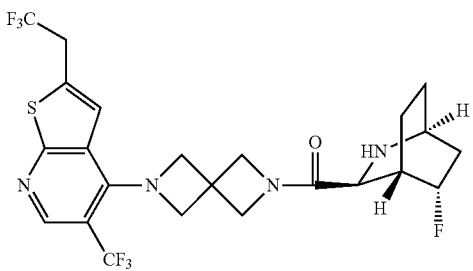

Example 1

To a solution of tert-butyl (1S,3S,4S,5S)-5-fluoro-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octane-2-carboxylate (3.8 g) prepared in Reference example 9 in dichloromethane (20 mL) was added TFA (9.3 mL) at room temperature, and the mixture was stirred at room temperature for 3 hours. The solvent was removed in vacuo, and the residue was purified by amine silica gel column chromatography (ethyl acetate/methanol) to give the compound of Example 1 (3.0 g). ¹H-NMR (400 MHz, DMSO-d6) δ: 8.32 (1H, s), 7.66 (1H, s), 4.92 (1H, m), 4.72 (4H, dd, J=26.1, 11.9 Hz), 4.38 (2H, dd, J=40.1, 9.4 Hz), 4.13 (2H, dd, 25.0, 10.8 Hz), 4.05 (2H, dd, J=22.2, 11.2 Hz), 2.87 (1H, s), 2.76 (1H, s), 2.11-2.00 (2H, m), 1.72 (1H, dd, J=37.6, 13.8 Hz), 1.59-1.48 (2H, m), 1.35-1.23 (2H, m). LC-MS; [M+H]²⁻269.4/Rt (min) 0.76

Examples 2-27

The following Examples 2 to 27 were prepared according to a similar method to Example 1 by using each corresponding starting compound.

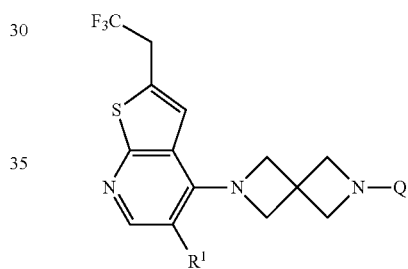

| Example | R¹ | Q | LC-MS: [M + H]⁺ or [M + 2H]²⁺/Rt (min); ¹H-NMR |
|---|---|---|---|
| 2 | CF₃ | 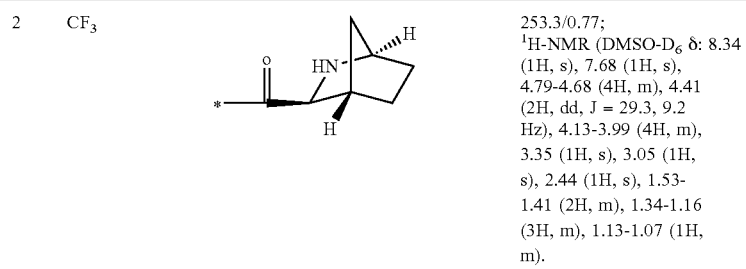 | 253.3/0.77; ¹H-NMR (DMSO-D₆ δ: 8.34 (1H, s), 7.68 (1H, s), 4.79-4.68 (4H, m), 4.41 (2H, dd, J = 29.3, 9.2 Hz), 4.13-3.99 (4H, m), 3.35 (1H, s), 3.05 (1H, s), 2.44 (1H, s), 1.53-1.41 (2H, m), 1.34-1.16 (3H, m), 1.13-1.07 (1H, m). |
| 3 | CF₃ | 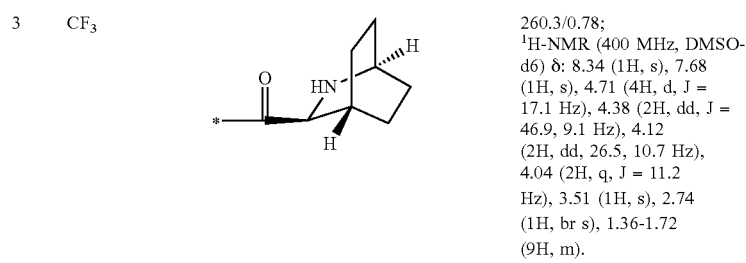 | 260.3/0.78; ¹H-NMR (400 MHz, DMSO-d6) δ: 8.34 (1H, s), 7.68 (1H, s), 4.71 (4H, d, J = 17.1 Hz), 4.38 (2H, dd, J = 46.9, 9.1 Hz), 4.12 (2H, dd, 26.5, 10.7 Hz), 4.04 (2H, q, J = 11.2 Hz), 3.51 (1H, s), 2.74 (1H, br s), 1.36-1.72 (9H, m). |

-continued

| Example | R¹ | Q | LC-MS: [M + H]⁺ or [M + 2H]²⁺/Rt (min); ¹H-NMR |
|---|---|---|---|
| 4 | CF₃ | | 278.2/0.86; ¹H-NMR (400 MHz, DMSO-d6) δ: 8.34 (1H, s), 7.66 (1H, s), 4.92 (1H, m), 4.77-4.71 (4H, m), 4.44 (2H, dd, J = 14.4, 9.5 Hz), 4.15 (2H, dd, 22.3, 10.1 Hz), 4.05 (2H, q, J = 11.0 Hz), 3.75 (1H, br s), 3.13 (1H, br s), 2.28-1.98 (3H, m), 1.65-1.54 (3H, m), 1.46-1.39 (1H, m). |
| 5 | CF | | 275.3/0.90 |
| 6 | CF₃ | | 268.2/0.75; ¹H-NMR (400 MHz, DMSO-d6) δ: 8.34 (1H, s), 7.68 (1H, s), 4.73 (2H, br s), 4.69 (2H, br s), 4.61 (1H, d, J = 3.7 Hz), 4.38 (2H, dd, J = 43.7, 9.5 Hz), 4.16-4.00 (4H, m), 3.82 (1H, m), 3.36 (1H, br s), 2.55 (1H, br s), 2.02 (1H, m), 1.81 (1H, m), 1.72 (1H, br s), 1.41-1.23 (4H, m). |
| 7 | CF₃ | | 268.2/0.73 |
| 8 | CF₃ | | 267.3/0.75; ¹H-NMR (400 MHz, DMSO-d6) δ: 8.34 (1H, s), 7.66 (1H, s), 4.77-4.69 (4H, m), 4.40 (2H, dd, J = 29.6, 9.5 Hz), 4.15 (2H, q, 10.8 Hz), 4.05 (2H, q, J = 11.0 Hz), 3.78 (1H, s), 3.28 (1H, s) 2.44-2.23 (3H, m), 1.78 (2H, m), 1.56 (2H, m). |
| 9 | CF₃ | | 262.7/0.70; ¹H-NMR (CDCl₃) δ: 8.42 (1H, s), 7.33 (1H, s), 5.19-4.99 (1H, m), 4.80-4.64 (4H, m), 4.44 (2H, dd, J = 44.0, 9.2 Hz), 4.25 (2H, dd, J = 31.8, 9.1 Hz), 3.87 (1H, s), 3.67-3.51 (3H, m), 2.73-2.68 (1H, m), 2.05-1.92 (1H, m), 1.63-1.29 (3H, m). |
| 10 | CF₃ | | 269.2/0.82; ¹H-NMR (400 MHz, DMSO-d6) δ: 8.34 (1H s), 7.68 (1H, s), 4.88 (0.5H, m), 4.71 (4.5H, m), 4.41 (2H, dd, J = 35.8, 9.5 Hz), 4.14 (2H, m), 4.05 (2H, dd, J = 22.3, 11.3 Hz), |

-continued

| Example | R¹ | Q | LC-MS: [M + H]⁺ or [M + 2H]²⁺/Rt (min); ¹H-NMR |
|---|---|---|---|
| | | | 3.39 (1H, br s), 2.93 (1H, br s), 2.15 (1H, m), 1.90 (1H, m), 1.68-1.39 (4H, m), 1.22 (1H, m). |
| 11 | CF₃ | (structure) | 288.3/0.93; ¹H-NMR (DMSO-D₆) δ: 8.34 (1H, s), 7.68 (1H, s), 5.91-5.82 (1H, m), 5.23 (1H, d, J = 17.2 Hz), 5.10 1H, d, J = 8.8 Hz), 4.73-4.68 (4H, m), 4.39 (2H, dd, J = 29.3, 9.2 Hz), 4.16-4.00 (4H, m), 3.91 (1H, d, J = 5.6 Hz), 3.70-3.60 (1H, m), 3.39 (1H, s), 3.30 (3H, s), 2.88-2.83 (1H, s), 2.10-2.15 (1H, m), 1.79-1.60 (2H, m), 1.45-1.30 (4H, m). |
| 12 | CF₃ | (structure) | 288.3/0.92 |
| 13 | CF₃ | (structure) | 625.4/0.93; ¹H-NMR (DMSO-D₆ δ: 8.34 (1H, s), 7.68 (1H, s), 7.35-7.25 (5H, m), 4.73-4.68 (4H, m), 4.45 (2H, s), 4.39 (2H, dd, J = 29.3, 9.2 Hz), 4.16-4.00 (4H, m), 3.72-3.67 (1H, m) 3.39 (1H, s), 3.30 (3H, s), 2.91 (1H, s), 2.10-2.01 (1H, m), 1.80-1.75 (2H, m), 1.47-1.38 (4H, m). |
| 14 | CF₃ | (structure) | 625.4/0.90 |
| 15 | CF₃ | (structure) | 278.2/0.91 |
| 16 | CF₃ | (structure) | 267.2/0.75 |
| 17 | CF₃ | (structure) | 275.3/0.83 |

-continued

| Example | R¹ | Q | LC-MS: [M + H]⁺ or [M + 2H]²⁺/Rt (min); ¹H-NMR |
|---|---|---|---|
| 18 | CF₃ | | 313.3/1.17 |
| 19 | CF₃ | | 268.3/0.85 |
| 20 | CN | | 238.7/0.68 |
| 21 | CN | | 231.7/0.65 |
| 22 | CN | | 247.8/0.73 |
| 23 | CN | | 512.2/0.57 |
| 24 | CN | | 253.8/0.71 |
| 25 | CN | | 490.1/0.55 |
| 26 | CHF₂ | | 251.3/0.66 |

| Example | R¹ | Q | LC-MS: [M + H]⁺ or [M + 2H]²⁺/Rt (min); ¹H-NMR |
|---|---|---|---|
| 27 | CHF$_2$ | (structure) | 244.2/0.72 |

Tests

Test 1: Test for Evaluating the Inbinition of the Menin-MLL Binding

Menin$_{1-615}$ wherein 6× His tag and HA tag are inserted in the N-terminus, and myc tag is inserted in the C-terminus (hereinafter, referred to as His-Menin$_{1-615}$), was diluted with an assay buffer (25 mmol/L HEPES, 150 mmol/L NaCl, 1 mmol/L dithiothreitol, 0.5% (w/v) Tween 80, 0.3% (w/v) BSA, 0.3% (w/v) skim milk) to adjust the final concentration Lo 30 nmol/L. The test compounds were also diluted with the assay buffer to adjust each concentration of the test compounds to 0.005 to 5 μmol/L. The prepared His-Menin$_{1-615}$ and test compounds were added to a light-shielding 384-well low-volume plate (Corning, #4514) in 2 μL/well and 6 μL/well, respectively, and the plate was covered with a lid for light-shielding (Corning, r-3935), and incubated at room temperature for 3 hours. After the incubation, MLL$_{1-172}$ wherein FLAG tag is inserted in the C-terminus (MLL$_{1-172}$-FLAG), was separately diluted with the assay buffer to adjust the final concentration to 50 nmol/L. The prepared MLL$_{1-172}$-FLAG was added to the above plate in 2 μL/well, and the plate was covered with a lid for light-shielding and incubated at room temperature for an hour.

Then, anti-6HIS-d2 antibody (cisbio, 61HISDLA) and anti-FLAGM2-K antibody (cisbio, 61FG2KLA) were diluted with an antibody dilution buffer (50 mmol/L Tris, 150 mmol/L NaCl, 800 mmol/L KF, pH 7.4) to adjust the final concentration to 1.4 μg/mL to prepare an antibody mixture. The prepared antibody mixture was added to the above plate in 10 μL/well, and the plate was covered with a lid and incubated at 4° C. for 17 to 24 hours. After the incubation, the signal was detected with RUBYstar (BMG LABTECH). The binding inhibition rate (%) at each concentration of the test compounds was calculated from the following formula, and the IC$_{50}$ value was obtained, that corresponds to the concentration of the test compound at which the binding inhibition rate is 50%.

Binding inhibition rate (%)={1-(A-C)/(B-C)}×100

A: Signal in the presence of test compound
B: Signal of negative control (in the absence of test compound)
C: Signal of positive control (in the presence of known compound at the concentration which shows 100% inhibition ratio)

The results of the evaluation in Test 1 are shown in the following table.

| Example | HTRF IC$_{50}$ (nM) |
|---|---|
| 1 | 13.3 |
| 2 | 17.8 |
| 3 | 31.8 |
| 4 | 139.6 |
| 6 | 27.3 |
| 7 | 247.5 |
| 8 | 635.3 |
| 9 | 31.7 |
| 10 | 343.3 |
| 11 | 53.9 |
| 12 | 519.1 |
| 13 | 134.3 |
| 14 | 2400.2 |
| 20 | 11.4 |
| 21 | 8.4 |
| 22 | 6.2 |
| 23 | 11.0 |
| 25 | 90.2 |
| 26 | 44.7 |
| 27 | 26.0 |

The compounds of Examples 1, 2, 3, 6, 9, 11, 20, 21, 22, 23, 25, 26, and 27 showed potent Menin-MLL binding inhibition activity as shown in the above table.

Test 2: Test for Evaluating the Inhibition of Cell Proliferation

RS4; 11 cells were obtained from American Type Culture Collection (ATCC). The cells were cultured at 37° C. in the presence of 5% CO$_2$ in RPMI 1640 medium containing 10% fetal bovine serum and 1% penicillin/streptomycin. MOLM-13 cells were separately obtained from DSMZ. The cells were cultured at 37° C. in the presence of 5% CO$_2$ in RPMI 1640 medium containing 20% fetal bovine serum and 1% penicillin/streptomycin.

The cells were plated to a 96-well plate in 2000 cells/well, each test compound was added thereto to adjust the final concentration of DMSO to 0.1% of DMSO, and the cells were cultured for 7 days. After the cultivation, the cell viability was calculated with PrestoBlue™ Cell Viability Reagent (Invitrogen, A13261). The IC$_{50}$ value was calculated from a survival curve, that corresponds to the concentration of the test compound at which the cell proliferation inhibition rate is 50%. The results of the evaluation in Test 2 are shown in the following table.

| | IC$_{50}$ (μM) | |
|---|---|---|
| Example | RS4; 11 | MOLM-13 |
| 1 | 0.09 | 0.08 |
| 2 | 0.20 | 0.26 |
| 3 | 0.20 | 0.21 |
| 4 | 0.78 | 1.70 |
| 5 | 2.30 | >3.00 |
| 6 | 0.58 | 0.83 |
| 7 | 2.20 | 2.30 |
| 8 | 0.33 | 1.10 |
| 9 | 0.17 | 0.28 |
| 10 | 0.81 | 2.10 |
| 11 | 0.63 | 0.73 |

| | IC$_{50}$ (μM) | |
|---|---|---|
| Example | RS4; 11 | MOLM-13 |
| 12 | 1.80 | 2.20 |
| 13 | 0.62 | 0.81 |
| 14 | 1.20 | 2.20 |
| 15 | 1.50 | >3.00 |
| 16 | 2.30 | 1.90 |
| 17 | 2.60 | 3.00 |
| 18 | 2.10 | >3.00 |
| 19 | >3.00 | 2.50 |
| 20 | 0.27 | 0.22 |
| 21 | 0.27 | 0.24 |
| 22 | 0.10 | 0.09 |
| 23 | 0.28 | 0.29 |
| 25 | 0.69 | 2.20 |
| 26 | 0.29 | 0.68 |
| 27 | 0.56 | 0.94 |

The compounds of Examples 1, 2, 3, 4, 6, 8, 9, 10, 11, 13, 20, 21, 22, 23, 25, 26, and 27 showed good cell proliferation inhibition activity as shown in the above table. Especially, the compounds of Examples 1, 2, 3, 9, 20, 21, 22, and 23 showed potent cell proliferation inhibitory activity.

Test 3: Test for the Inhibition of mRNA Transcription with Test Compounds

MV4; 11 cells were obtained from American Type Culture Collection (ATCC). The cells were cultured at 37° C. in the presence of 5% CO$_2$ in RPMI 1640 medium containing 10% fetal bovine serum and 1% penicillin/streptomycin. To the MV4; 11 cells was added each test compound to adjust the final concentration to 1 μmol/L, and the cells were cultured at 37° C. in the presence of 5% CO$_2$ for 20 to 24 hours. After the incubation, the total RNA was extracted from the cells with RNeasy™ Mini Kit (QIAGEN, 74106), and cDNA was synthesized with Superscript™ VILO™ cDNA Synthesis Kit (Invitrogen, #11754250). By using TaqMan™ Gene Expression Master Mix (Applied Biosystems, 4369016) and TaqMan™ probe (Applied Biosystems), the expression level of mRNA was quantified from the obtained cDNA with 7900HT (Applied biosystems). The mRNA expression level of each obtained gene was fitted with the expression level of mRNA of GAPDH.

The results of the evaluation in Test 3 are shown in the following table.

| | mRNA at 1 μM (% control) | |
|---|---|---|
| Example | MEIS1 | HOXA9 |
| 1 | 18.0 | 43.3 |
| 2 | 32.0 | 34.3 |
| 3 | 18.7 | 32.0 |
| 4 | 65.4 | 60.0 |
| 6 | 51.3 | 54.3 |
| a | 82.9 | 79.3 |
| 9 | 34.2 | 49.4 |
| 10 | 68.8 | 69.5 |
| 11 | 60.7 | 64.5 |
| 13 | 57.3 | 63.0 |
| 20 | 41.8 | 59.3 |
| 21 | 40.9 | 52.1 |
| 22 | 18.1 | 37.0 |
| 23 | 45.4 | 49.3 |
| 26 | 41.4 | 57.6 |
| 27 | 48.9 | 53.5 |

The compounds of Examples 1, 2, 3, 4, 6, 8, 9, 10, 11, 13, 20, 21, 22, 23, 26, and 27 showed the mRNA transcription inhibition activity which is caused by the binding inhibition of Menin and MLL.

Test 4: Pharmacokinetic Study

The test compound suspended in 0.5% methylcellulose was orally administered to 7-week-old male SD rat in a dose of 10 mg/kg. The blood sample was taken from jugular vein without anesthesia over time for 24 hours. The blood sample was centrifuged to obtain plasma. The plasma was pre-treated by methanol extraction method, and then analyzed with an LC-MS/MS to determine the concentration of the test compound. Based on the data from 0 hour after the administration until the time (t) when there was the final detection in the plasma, AUC was calculated by trapezoidal method. The evaluation result of Test 4 is shown in the following table.

| Example | AUC$_{0-t}$ (ng · hr/mL) |
|---|---|
| 1 | 2413 |
| 2 | 1965 |
| 3 | 1206 |
| 9 | 3754 |
| 22 | 244 |
| 23 | 668 |

As shown in the above table, particularly Examples 1, 2, 3, and 9 showed good compound-exposure in plasma.

INDUSTRIAL APPLICABILITY

The compounds of the present invention can inhibit the binding of a MLL fusion protein and menin to provide the antitumor effect.

The invention claimed is:
1. A compound of formula (1):

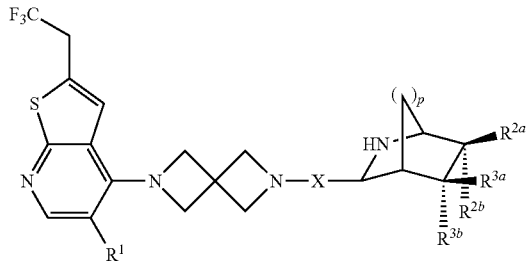

or a pharmaceutically acceptable salt thereof, wherein
p is 1 or 2,
$R^1$ is —CF$_3$, —CHF$_2$, or cyano,
$R^{2a}$, $R^{2b}$, $R^{3a}$, and $R^{3b}$ are each independently hydrogen atom, halogen atom, C$_{1-6}$ alkyl, C$_{2-6}$ alkenyl, C$_{2-6}$ alkynyl, C$_{3-10}$ cycloalkyl, —OR$^4$, 3- to 10-membered saturated heterocyclyl, C$_{6-10}$ aryl, or 5- to 12-membered heteroaryl (wherein the alkyl may be substituted with 1-3 fluorine atoms; the cycloalkyl and the saturated heterocyclyl are each independently substituted with the same or different 1-5 substituents selected from the group consisting of fluorine atom and C$_{1-3}$ alkyl; and the aryl and the heteroaryl are each independently substituted with the same or different 1-5 substituents selected from the group consisting of fluorine atom, chlorine atom, bromine atom, and C$_{1-3}$ alkyl); or $R^{2a}$ and $R^{2b}$ may be combined together to form =O, and $R^{3a}$ and $R^{3b}$ may be combined together to form =O, R⁴ is, each independently if there are plural, hydrogen atom, $C_{1-6}$ alkyl, $C_{2-6}$ alkenyl, $C_{2-6}$ alkynyl, $C_{3-10}$ cycloalkyl, 3- to 10-membered saturated heterocyclyl, $C_{6-10}$ aryl, or 5- to 12-membered heteroaryl (wherein the alkyl may be substituted with the same or different 1-5 substituents selected from the group consisting of $C_{3-10}$ cycloalkyl, 3- to 10-membered saturated heterocyclyl, $C_{6-10}$ aryl, and 5- to 12-membered heteroaryl; the cycloalkyl and the saturated heterocyclyl may be each independently substituted with the same or different 1-5 substituents selected from the group consisting of fluorine atom and $C_{1-3}$ alkyl; and the aryl and the heteroaryl may be each independently substituted with the same or different 1-5 substituents selected from the group consisting of fluorine atom, chlorine atom, bromine atom, and $C_{1-3}$ alkyl), and X is C(=O)— or $C_{1-6}$ alkylene.

2. The compound of claim 1 or a pharmaceutically acceptable salt thereof, wherein X is —C(=O)—, and R¹ is —CF₃.

3. The compound of claim 1 or a pharmaceutically acceptable salt thereof, wherein
R²ᵃ, R²ᵇ, R³ᵃ, and R³ᵇ are each independently hydrogen atom, fluorine atom, $C_{1-6}$ alkyl, or —OR⁴; or R²ᵃ and R²ᵇ may be combined together to form =O, and R³ᵃ and R³ᵇ may be combined together to form =O, and
R⁴ is, each independently if there are plural, hydrogen atom, $C_{2-6}$ alkenyl, or $C_{1-6}$ alkyl (wherein the alkyl may be substituted with $C_{6-10}$ aryl).

4. The compound of claim 1 or a pharmaceutically acceptable salt thereof, wherein formula (1) is the following formula (1-A):

(1-A)

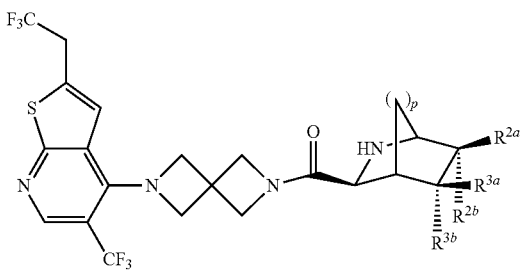

wherein
p is 1 or 2,
R²ᵃ and R²ᵇ are each independently hydrogen atom, fluorine atom, or —OR⁴,
R³ᵃ and R³ᵇ are each independently hydrogen atom or fluorine atom, or R³ᵃ and R³ᵇ may be combined together to form =O, and
R⁴ is, each independently if there are plural, hydrogen atom, $C_{2-4}$ alkenyl, or $C_{1-3}$ alkyl (wherein the alkyl may be substituted with phenyl).

5. The compound of claim 1 or a pharmaceutically acceptable salt thereof, wherein
R²ᵃ and R²ᵇ are hydrogen atom, and
R³ᵃ and R³ᵇ are each independently hydrogen atom or fluorine atom.

6. The compound of claim 1 or a pharmaceutically acceptable salt thereof, wherein R³ᵃ is hydrogen atom, and R³ᵇ is fluorine atom.

7. The compound of claim 1 or a pharmaceutically acceptable salt thereof, wherein the compound is selected from the following:
{(1S,3S,4S,5S)-5-fluoro-2-azabicyclo[2.2.2]octan-3-yl}{6-[2- (2,2,2-trifluoroethyl)-5-(trifluoromethyl) thieno[2,3-b]pyridin-4-yl]-2,6-diazaspiro [3.3]heptan-2-yl}methanone,
[(1R,3S,4S)-2-azabicyclo [2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone,
[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone,
[(1S,3S,4S)-5, 5-difluoro-2-azabicyclo[2.2.2]octan-3-yl]{6-[2(2,2,2-trifluoroethyl)-5-(trifluoromethyl)thieno[2,3-b]pyridin-4-yl]-2,6-diazaspiro [3.3]heptan-2-yl)methanone,
[1S,3S,4R,6S)-6-hydroxy-2-azabicyclo [2.2.2]octan-3-yl]{6-[2-(2,2,2-trifluoroethyl)-5-(trifluoromethyl)thieno [2,3-b]pyridin-4-yl]-2, 6-diazaspiro [3.3]heptan-2-yl}methanone,
(1S,3S,4S)-3-{6-[2-(2,2,2-trifluoroethyl)-5-(trifluoromethyl)thieno[2,3-b]pyridin-4-yl]-2,6-diazaspiro[3.3] heptane-2-carbonyl}-2-azabicyclo[2.2.2]octan-5-one,
[(1S,3S,4S,5S)-5-fluoro-2-azabicyclo[2.2.1]heptan-3-yl] {6[2-(2,2,2-trifluoroethyl)-5-(trifluoromethyl)thieno[2, 3-b]pyridin-4-yl]-2,6-diazaspiro [3.3]heptan-2-yl}methanone,
[(1S,3S,4R,6R)-6-fluoro-2-azabicyclo[2.2.2]octan-3-yl] {6[2-(2,2,2-trifluoroethyl)-5-(trifluoromethyl)thieno[2, 3-b]pyridin-4-yl]-2,6-diazaspiro [3.3]heptan-2-yl}methanone,
{(1S,3S,4R,6S)-6-[(prop-2-en-1-yl)oxy]-2-azabicyclo [2.2.2]octan-3-yl}{6-[2-(2,2,2-trifluoroethyl)-5-(trifluoromethyl)thieno[2,3-b]pyridin-4-yl]-2,6-diazaspiro [3.3]heptan-2-yl}methanone,
[(1S,3S,4R,6S)-6-(benzyloxy)-2-azabicyclo [2.2.2]octan-3-yl]}6-[2-(2,2,2-trifluoroethyl)-5-(trifluoromethyl) thieno[2,3-b]pyridin-4-yl]-2,6-diazaspiro [3.3]heptan-2-yl}methanone,
4-{6-[3S)-2-azabicyclo[2.2.2]octane-3-carbonyl]-2,6-diazaspiro[3.3]heptan-2-yl}-2-(2,2,2-trifluoroethyl) thieno[2,3-b]pyridine-5-carbonitrile,
4-{6-[(1R,3S,4S)-2-azabicyclo[2.2.1]heptane-3-carbonyl]-2,6-diazaspiro[3.3]heptan-2-yl}-2-(2,2,2-trifluoroethyl)thieno[2,3-b]pyridine-5-carbonitrile,
4-{6-[(1S,3S,4S,5S)-5-fluoro-2-azabicyclo[2.2.2]octane-3-carbonyl]-2,6-diazaspiro[3.3]heptan-2-yl}-2-(2,2,2-trifluoroethyl)thieno[2,3-b]pyridine-5-carbonitrile,
4-{6-[(1S,3S,4S)-5,5-difluoro-2-azabicyclo[2.2.2]octane-3-carbonyl]-2,6-diazaspiro[3.3]heptan-2-yl{-2-(2,2,2-trifluoroethyl)thieno[2,3-b]pyridine-5-carbonitrile,
4-{6-[(1S,3S,4S)-5-oxo-2-azabicyclo[2.2.2]octane-3-carbonyl]-2,6-diazaspiro[3.3]heptan-2-yl-2-(2,2,2-trifluoroethyl)thieno[2,3-b]pyridine-5-carbonitrile,
[(3S)-2-azabicyclo[2.2.2]octan-3-yl]{6-[5-(difluoromethyl)-2-(2,2,2-trifluoroethyl)thieno[2,3-b]pyridin-4-yl]-2,6-diazaspiro[3.3]heptan-2-yl}methanone, and
[(1R,3S 4S)-2-azabicyclo [2.2.1]heptan-3-yl]{6-[5-(difluoromethyl)-2-(2,2,2-trifluoroethyl)thieno [2,3-b] pyridin-4-yl]-2, 6-diazaspiro [3.3]heptan-2-yl}methanone.

8. The compound of claim 1 or a pharmaceutically acceptable salt thereof, wherein the compound is selected from the following:

{(1S,3S,4S,5S)-5-fluoro-2-azabicyclo[2.2.2]octan-3-yl}{6(2,2,2-trifluoroethyl)-5-(trifluoromethyl)thieno[2,3-b]pyridin-4-yl]-2,6-diazaspiro [3.3]heptan-2-yl}methanone,
[(1R,3S,4S)-2-azabicyclo [2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone,
[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone,
[(1S,3S,4S)-5,5-difluoro-2-azabicyclo[2.2.2]octan-3-yl]{6-[2(2,2,2-trifluoroethyl)-5-(trifluoromethyl)thieno[2,3-b]pyridin-4-yl]-2,6-diazaspiro [3.3]heptan-2-yl}methanone,
[1S,3S,4R,6S)-6-hydroxy-2-azabicyclo [2.2.2]octan-3-yl]{6-[2-(2,2,2-trifluoroethyl)-5-(trifluoromethyl)thieno[2,3-b]pyridin-4-yl]-2,6-diazaspiro [3.3]heptan-2-yl}methanone,
(1S,3S,4S)-3-{6-[2-(2,2,2-trifluoroethyl)-5-(trifluoromethyl)thieno[2,3-b]pyridin-4-yl]-2,6-diazaspiro[3.3]heptane-2-carbonyl}-2-azabicyclo[2.2.2]octan-5-one,
[(1S,3S,4S,5S)-5-fluoro-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro [3.3]heptan-2-yl}methanone,
[(1S,3S,4R,6R)-6-fluoro-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro [3.3]heptan-2-yl}methanone,
{(1S,3S,4R,6S)-6-[(prop-2-en-1-yl)oxy]-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone, and
[(1S,3S,4R,6S)-6-(benzyloxy)-2-azabicyclo[2.2.2]octan-3-yl]}6-[2-(2,2,2-trifluoroethyl)-5-(trifluoromethyl)thieno[2,3-b]pyridin-4-yl]-2,6-diazaspiro[3.3]heptan-2-yl}methanone.

9. The compound of claim 1 or a pharmaceutically acceptable salt thereof, wherein the compound is selected from the following:
{(1S,3S,4S,5S)-5-fluoro-2-azabicyclo[2.2.2]octan-3-yl}{6-[2-(2,2,2-trifluoroethyl)-5-(trifluoromethyl)thieno[2,3-b]pyridin-4-yl]-2,6-diazaspiro[3.3]heptan-2-yl}methanone,
[(1R,3S,4S)-2-azabicyclo [2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone,
[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone, and
[(1S,3S,4S,5S)-5-fluoro-2-azabicyclo[2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone.

10. The compound of claim 1 or a pharmaceutically acceptable salt thereof, wherein the compound is the following:
}(1S,3S,4S,5S)-5-fluoro-2-azabicyclo[2.2.2]octan-3-yl}{6-[2-(2,2,2-trifluoroethyl)-5-(trifluoromethyl)thieno [2,3-b]pyridin-4-yl]-2,6-diazaspiro[3.3]heptan-2-yl}methanone.

11. The compound of claim 1 or a pharmaceutically acceptable salt thereof, wherein the compound is the following:
[(1R,3S,4S)-2-azabicyclo [2.2.1]heptan-3-yl]{6-[2-(2,2,2-trifluoroethyl)-5-(trifluoromethyl)thieno[2,3-b]pyridin-4-yl]-2,6-diazaspiro[3.3]heptan-2-yl methanone.

12. The compound of claim 1 or a pharmaceutically acceptable salt thereof, wherein the compound is the following:
[(3S)-2-azabicyclo[2.2.2]octan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone.

13. The compound of claim 1 or a pharmaceutically acceptable salt thereof, wherein the compound is the following:
[(1S,3S,4S,5S)-5-fluoro-2-azabicyclo[2.2.1]{heptan-3-yl]{6-[2-(2,2,2-trifluoroethyl)-5-(trifluoromethyl)thieno[2,3-b]pyridin-4-yl]-2,6-diazaspiro[3.3]heptan-2-yl}methanone.

14. A pharmaceutical composition comprising the compound of claim 1 or a pharmaceutically acceptable salt thereof.

15. A pharmaceutical composition comprising the compound of claim 1 or a pharmaceutically acceptable salt thereof in combination with at least one compound selected from the group consisting of an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other anticancer medicaments.

16. A method of treating a tumor associated with menin-MLL interaction comprising administering a compound of claim 1 or a pharmaceutically acceptable salt thereof.

17. The method of claim 16, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic lymphocytic leukemia, chronic myeloid leukemia, myelodysplastic syndrome, polycythemia vera, malignant lymphoma (including B-cell lymphoma), myeloma (including multiple myeloma), brain tumor, cancer of the head and neck, esophageal cancer, thyroid cancer, small cell lung cancer, non-small cell lung cancer, breast cancer, gastric cancer, gallbladder and bile duct cancer, liver cancer, hepatocellular cancer, pancreatic cancer, colon cancer, rectal cancer, anal cancer, chorionepithelioma, endometrial cancer, cervical cancer, ovarian cancer, bladder cancer, urothelial cancer, renal cancer, renal cell cancer, prostate cancer, testicular tumor, testicular germ cell tumor, ovarian germ cell tumor, Wilms' tumor, malignant melanoma, neuroblastoma, osteosarcoma, Ewing's sarcoma, chondrosarcoma, soft tissue sarcoma, or skin cancer.

18. The method of claim 16, wherein the tumor is acute leukemia (including MLL acute leukemia, MLL partial tandem duplicate acute leukemia, NPM mutated acute leukemia, MOZ acute leukemia, NUP98 acute leukemia, and CALM acute leukemia), chronic myeloid leukemia, malignant lymphoma (including B-cell lymphoma), myeloma (including multiple myeloma), brain tumor, prostate cancer, breast cancer, neuroblastoma, Ewing's sarcoma, or liver cancer.

19. The method of claim 16 wherein the tumor is MLL acute leukemia, MLL partial tandem duplicate acute leukemia, NPM mutated acute leukemia, MOZ acute leukemia, NUP98 acute leukemia, CALM acute leukemia, chronic myeloid leukemia, B-cell lymphoma, multiple myeloma, neuroblastoma, or prostate cancer.

20. The method of claim 16 wherein the tumor is MLL acute leukemia, or NPM mutated acute leukemia.

21. The method of claim 16 wherein the tumor is accompanied by high expression of HOXa gene cluster, or MEIS gene cluster.

22. The method of claim 16 wherein the tumor is accompanied by p53 gain-of-function mutation.

23. The the method of claim 16 wherein the compound is administered in combination with at least one member selected from the group consisting of from an anticancer alkylating agent, an anticancer antimetabolite, an anticancer antibiotic, a plant-derived anticancer medicament, an anticancer platinum complex compound, an anticancer camptothecin derivative, an anticancer tyrosine kinase inhibitor, an anticancer serine/threonine kinase inhibitor, an anticancer phospholipid kinase inhibitor, an anticancer monoclonal antibody, interferon, a biological response modifier, a hormone preparation, an angiogenic inhibitor, an immune checkpoint inhibitor, an epigenetics-associated molecular inhibitor, a protein post-translational modification inhibitor, a proteasome inhibitor, and other antitumor medicament.

* * * * *